(12) United States Patent
Arnold et al.

(10) Patent No.: US 8,385,731 B2
(45) Date of Patent: Feb. 26, 2013

(54) HEAT EXCHANGER FOR HIGH FLOW RATE INFUSION

(75) Inventors: Randall C. Arnold, Minnetonka, MN (US); Mark T. Bieberich, Edina, MN (US); Gary L. Hansen, Eden Prairie, MN (US); Andrew J. McGregor, Minnetonka, MN (US); Christopher A. Miller, Apple Valley, MN (US); Donald E. Stapf, Minneapolis, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

(21) Appl. No.: 13/135,278

(22) Filed: Jun. 30, 2011

(65) Prior Publication Data

US 2011/0270180 A1 Nov. 3, 2011

Related U.S. Application Data

(63) Continuation of application No. 12/661,113, filed on Mar. 11, 2010, now Pat. No. 7,983,540, which is a continuation of application No. 11/789,515, filed on Apr. 24, 2007, now Pat. No. 7,720,362.

(51) Int. Cl.
*A61F 7/00* (2006.01)
(52) U.S. Cl. ......... 392/470; 392/465; 392/467; 604/113
(58) Field of Classification Search ............... None
See application file for complete search history.

(56) References Cited

U.S. PATENT DOCUMENTS

| | | | |
|---|---|---|---|
| 4,177,808 A | 12/1979 | Malbec | 604/122 |
| 4,493,705 A | 1/1985 | Gordon et al. | 604/122 |
| 4,568,330 A | 2/1986 | Kujawski et al. | 604/53 |
| 4,643,713 A | 2/1987 | Viitala | 604/4 |
| 4,734,269 A | 3/1988 | Clarke et al. | 422/310 |
| 4,818,186 A | 4/1989 | Pastrone et al. | 417/63 |
| 4,823,535 A | 4/1989 | Schmidt et al. | 53/284.4 |
| 4,863,452 A | 9/1989 | Irmiter et al. | 604/408 |
| 4,884,065 A | 11/1989 | Crouse et al. | 340/632 |
| 4,900,308 A | 2/1990 | Verkaart | 604/126 |
| 5,006,110 A | 4/1991 | Garrison et al. | 604/65 |
| 5,013,889 A | 5/1991 | Bakke | 692/470 |
| 5,061,236 A | 10/1991 | Sutherland et al. | 604/4 |
| 5,245,693 A | 9/1993 | Ford et al. | 392/470 |
| 5,381,510 A | 1/1995 | Ford et al. | 392/470 |
| 5,382,232 A | 1/1995 | Hague et al. | 604/65 |
| 5,591,251 A | 1/1997 | Brugger | 95/242 |

(Continued)

FOREIGN PATENT DOCUMENTS

EP 1159019 11/2002
WO WO 00/53246 9/2000

(Continued)

OTHER PUBLICATIONS

Fluido®—A Warm Revolution—A new generation in blood & fluid warming—User Manual, INT/R016—Feb. 2001-Jan. 2004, The Surgical Company International B.V.

(Continued)

*Primary Examiner* — Thor Campbell
(74) *Attorney, Agent, or Firm* — Adam M. Bramwell; Terrance A. Meador

(57) ABSTRACT

A heat exchanger has a laminar fluid flow path receivable between the heating plates of a high flow rate infusion unit to which heat is conducted by contact with the heating plates. A bubble trap and a valve are integrated with the heat exchanger. The bubble trap collects air from the infusate exiting the laminar flow path, and includes an air vent in contact with the infusate that vents the air from the bubble trap. The valve shuts off the flow of infusate if air is detected in the bubble trap.

13 Claims, 23 Drawing Sheets

U.S. PATENT DOCUMENTS

| | | | |
|---|---|---|---|
| 5,616,124 A | 4/1997 | Hague et al. | 604/65 |
| 5,674,199 A | 10/1997 | Brugger | 604/122 |
| 5,707,431 A | 1/1998 | Verkaart et al. | 96/177 |
| 5,720,728 A | 2/1998 | Ford | 604/131 |
| 5,807,332 A | 9/1998 | Augustine et al. | 604/113 |
| 5,840,068 A | 11/1998 | Cartledge | 604/131 |
| 5,935,105 A | 8/1999 | Manning et al. | 604/122 |
| 5,961,700 A | 10/1999 | Oliver | 96/158 |
| 6,047,108 A | 4/2000 | Sword et al. | 392/470 |
| 6,062,429 A | 5/2000 | West et al. | 222/95 |
| 6,142,974 A | 11/2000 | Kistner et al. | 604/113 |
| 6,236,809 B1 | 5/2001 | Cassidy et al. | 392/470 |
| 6,259,074 B1 | 7/2001 | Brunner et al. | 219/497 |
| 6,296,020 B1 | 10/2001 | McNeely et al. | 137/806 |
| 6,328,712 B1 | 12/2001 | Cartledge | 604/113 |
| 6,464,666 B1 | 10/2002 | Augustine et al. | 604/113 |
| 6,508,859 B1 | 1/2003 | Zia et al. | 95/46 |
| 6,535,689 B2 | 3/2003 | Augustine et al. | 392/470 |
| 6,554,791 B1 | 4/2003 | Cartledge et al. | 604/67 |
| 6,673,098 B1 | 1/2004 | Machold et al. | 607/96 |
| 6,775,473 B2 | 8/2004 | Augustine et al. | 392/470 |
| 6,827,862 B1 | 12/2004 | Brockhoff et al. | 210/787 |
| 6,942,637 B2 | 9/2005 | Cartledge et al. | 607/67 |
| 7,010,221 B2 | 3/2006 | Augustine et al. | 392/470 |
| 7,232,457 B2 | 6/2007 | Schmidt et al. | 607/96 |
| 7,316,666 B1 | 1/2008 | Entenman et al. | 604/113 |
| 7,720,362 B2 | 5/2010 | Arnold et al. | 392/470 |
| 2002/0147481 A1 | 10/2002 | Brugger et al. | 607/106 |
| 2004/0024342 A1 | 2/2004 | Weitzel et al. | 604/5.01 |
| 2004/0026068 A1 | 2/2004 | Schmidt et al. | 165/46 |
| 2004/0190885 A1 | 9/2004 | Entenman et al. | 392/470 |
| 2005/0148934 A1 | 7/2005 | Martens et al. | 604/113 |
| 2006/0211986 A1 | 9/2006 | Smisson, III et al. | 604/113 |
| 2006/0211988 A1 | 9/2006 | Smisson, III et al. | 604/122 |
| 2007/0173759 A1 | 7/2007 | Augustine et al. | 604/113 |
| 2008/0267599 A1 | 10/2008 | Arnold et al. | 392/470 |
| 2008/0269663 A1 | 10/2008 | Arnold et al. | 604/19 |
| 2008/0269676 A1 | 10/2008 | Bieberich et al. | 604/113 |
| 2008/0269679 A1 | 10/2008 | Arnold et al. | 604/122 |

FOREIGN PATENT DOCUMENTS

| | | |
|---|---|---|
| WO | WO 01/26719 A1 | 4/2001 |
| WO | WO 2008/130715 A2 | 10/2008 |

OTHER PUBLICATIONS

Thermacor 1200—Infusing Warmth in a Heartbeat—Overview, http://www.thermacor1200.com/thermacor-1200-overview.aspx, © 2007.

Level-1®—H-1200 Fast Flow Fluid Warmer—Operator's Manual, Part No. 4533706 GB Rev. A (Nov. 2003), Smiths Medical.

Smith, Charles E., et al., Evaluation of a new IV fluid and blood warming system to prevent air embolism. ITACCS Fall/Winter 2001.

Sessler, Daniel I., Complications and treatment of mild hypothermia. Anesthesiology, V. 95, No. 2, Aug. 2001, pp. 531-543.

Barcelona, Sandra L., et al., A comparison of flow rates and warming capabilities of the Level 1 and rapid infusion system with various-size intravenous catheters, Anesth. Analg. 2003;97:358-363.

Horowitz, Peter E., et al., Flow rates and warming efficiency with hotline and ranger blood/fluid warmers, Anesth. Analg. 2004;99:788-792.

International Search Report and Written Opinion, mailed Nov. 7, 2009 in PCT/US2008/005198, filed Apr. 23, 2008.

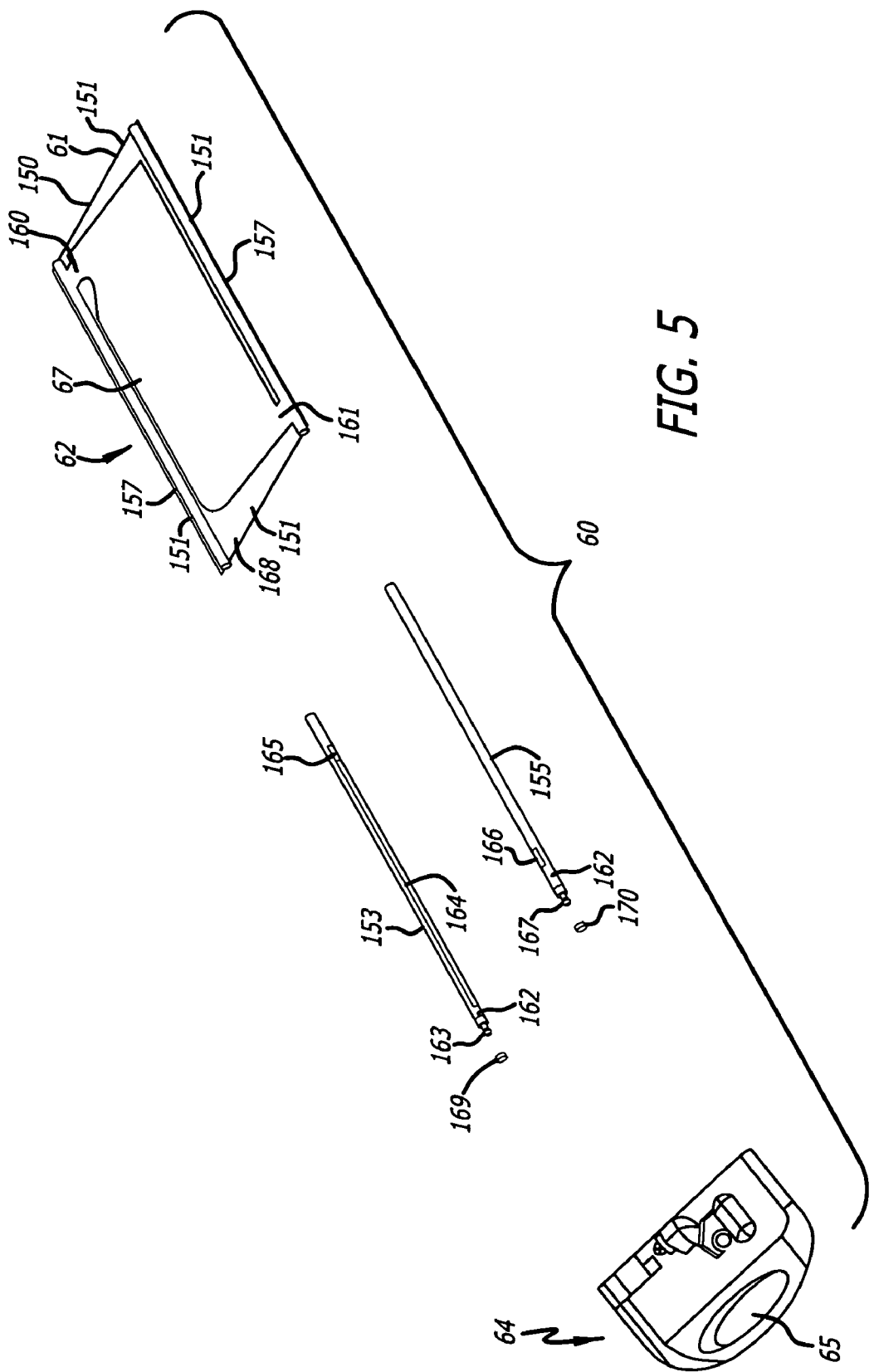

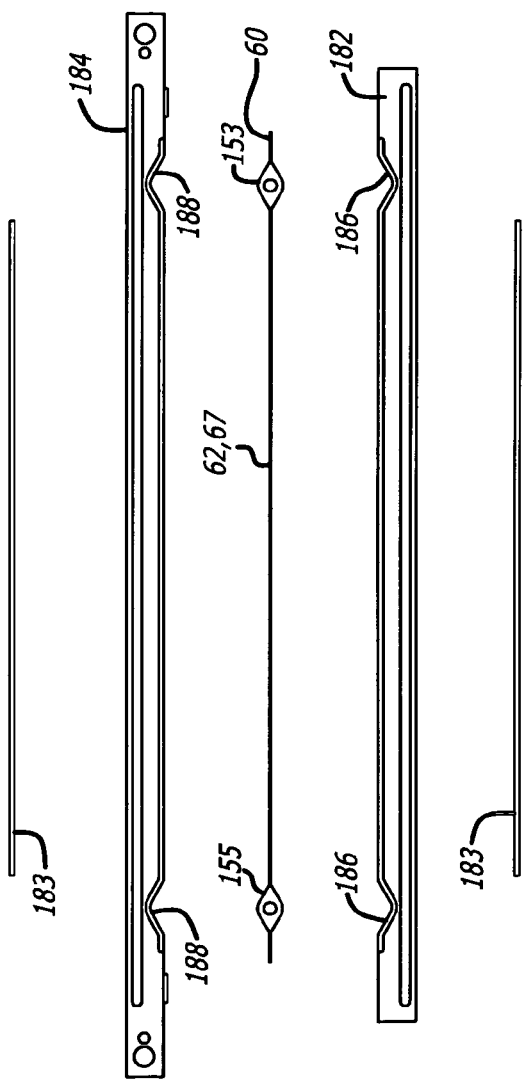

HEAT EXCHANGER FOR HIGH FLOW RATE INFUSION

PRIORITY

This patent application is a continuation of co-pending U.S. patent application Ser. No. 12/661,113, filed Mar. 11, 2010, which is a continuation of Ser. No. 11/789,515, filed Apr. 24, 2007, now U.S. Pat. No. 7,720,362, all commonly owned herewith.

CROSS REFERENCE TO RELATED APPLICATIONS

This patent application contains subject matter related to the following patent applications, all assigned to the assignee of this application:

U.S. patent application Ser. No. 10/214,966, filed Aug. 8, 2002, for "Fluid Warming Cassette with a Tensioning Rod", published as US 2004/0026068 A1 on Feb. 12, 2004, now U.S. Pat. No. 7,232,457;

U.S. patent application Ser. No. 10/397,942, filed Mar. 25, 2003, for "Fluid Warming Cassette and System Capable of Operation under Negative Pressure", published as US 2004/0190885 A1 on Sep. 30, 2004, now U.S. Pat. No. 7,394,976;

U.S. patent application Ser. No. 10/822,580, filed Apr. 12, 2004, for "Intravenous Fluid Warming Cassette with Rails and a Stiffening Member", now U.S. Pat. No. 7,316,666;

U.S. patent application Ser. No. 11/789,523, filed Apr. 24, 2007, for "High Flow Rate Infusion Unit and Heat Exchanger", published as US 2008/-269663 A1 on Oct. 30, 2008, now U.S. Pat. No. 7,927,302;

U.S. patent application Ser. No. 11/789,752, filed Apr. 24, 2007, for "Bubble Trap for High Flow Rate Infusion", published as US 2008/0269679 A1 on Oct. 30, 2008, now U.S. Pat. No. 7,803,217;

U.S. patent application Ser. No. 12/148,719, filed Apr. 22, 2008, for "High Flow Rate Infusion With Extraction Assist", published as US 2008/0269676 A1 on Oct. 30, 2008; and, PCT application PCT/US2008/05198, filed Apr. 23, 2008, for "High Flow Rate Infusion Unit and Heat Exchanger".

The assignee of this application now owns the following issued U.S. patents containing subject matter related to the subject matter of this application: U.S. Pat. Nos. 5,807,332; 6,464,666; 6,535,689; 6,775,473; and 7,010,221.

The assignee of this application now owns European Patent 1 159 019, granted Nov. 6, 2002 for "IV Fluid Warming System with Detection of Presence and Alignment of Cassette", which has been validated in Germany, France, Great Britain, Ireland, and Monaco.

See PCT application PCT/US20000/02630, filed Feb. 2, 2000 for "Pressure Tolerant Parenteral Fluid and Blood Container for a Warming Cassette", publication WO 01/26719, Apr. 19, 2001, filed by the assignee of this application.

BACKGROUND

The subject matter relates to heat exchanger for a high flow rate infusion unit that pressurizes and warm fluids for infusion into a body at pressures equal to or exceeding gravity.

Infusion relates to the introduction of a fluid into a body, usually, although not necessarily, into vasculature. A fluid that is infused into a body may be termed an "infusate". Such fluids may include, for example, blood, blood products, and solutions such as saline, antibiotics, and medications.

The combination of low operating room temperatures and the administration of anesthetics which inhibit a patient's thermoregulatory function leads to hypothermia during surgery. As is known, perioperative hypothermia can produce adverse outcomes such as surgical wound infection, extended hospitalization, and blood loss. See Sessler DI: Complications and Treatment of Mild Hypothermia. ANESTHESEOLOGY 2001; 95:531-543. Prevention or mitigation of hypothermia, particularly perioperative hypothermia, is thus a key clinical factor for successful treatment outcomes.

Hypothermia may be accelerated by infusion of fluid, especially if the fluid is refrigerated. For example, Sessler indicates that a unit of refrigerated blood or a liter of crystalloid solution at room temperature decreases the mean body temperature of adults by approximately 0.25° C. But patients suffering from serious trauma may require rapid infusion of large amounts of fluid, which can cause a sharp and sudden loss of heat in the body core, leading to a drop in mean core body temperature. In order to prevent or mitigate infusion-caused heat loss in a trauma patient, the infusate is often heated as it is administered.

Warming fluid prior to infusion into a human or animal body is known. See, for example the intravenous fluid warming systems and appliances described in the cross-referenced patent documents. See also the Ranger® blood/fluid warming system and products described at www.arizant.com, the web site of Arizant Healthcare Inc. The Ranger® blood/fluid warming system includes a heating appliance and a heat exchanger capable of being inserted into the heating appliance. Fluid flowing though the heat exchanger is warmed by contact between the heating appliance and heat exchanger, and then delivered intravenously to a patient. However, the disclosed systems cannot meet all rates of infusate delivery needed for treatment of trauma patients.

The technical challenges in heating a high volume of infusate delivered at a relatively high rate, for example, at 30 liters per hour (30 L/hr), or higher, include uniform transfer of heat to the fast-flowing fluid, elimination of air from the fluid, and an infusion system construction that supports convenience and speed of operation.

Solutions to these challenges in the prior state of the art include a known high speed infusion system that warms infusate by immersion of a heat exchanger in a warm water bath. A column of infusate flows through the heat exchanger, and the warm water bath heats the infusate as it passes through the heat exchanger. The heat, the flow pattern and high flow rate of the infusate create bubbles in the infusate, which must be removed before intravenous delivery in order to avoid formation of an air embolism in the patient being infused. This high speed infusion system includes a gas elimination device to collect bubbles from the infusate, and a clamp to halt the flow of infusate if air is detected in the infusate.

The known high speed infusion system is constituted of an appliance with a water heating and circulation system. The heat exchanger consists of a pair of coaxial tubes, a smaller one disposed inside a larger one. The infusate flows through the annulus between the larger and smaller tube, and the heated water is circulated from the heater, through the inner tube, and back to the heater. The heat exchanger is installed in the appliance where it must be reliably coupled to an infusate flow path and to a separate hot water flow path. The gas elimination device is separate from the heat exchanger; and it is installed separately and downstream from the heat exchanger. Infusate passes through the gas elimination device into a patient line for intravenous delivery to a patient. When a predetermined amount of air is detected in the gas elimination device, a downstream clamp is activated to pinch off the patient line, thereby stopping the flow of infusate to the patient. The heat exchanger and gas elimination device are discarded after each use, and new ones must be installed each time a patient is treated.

In this known high speed infusion system, the heat transfer mechanism poses a risk of an exchange of contaminants between the infusate and the water used to deliver heat. This may occur when the barrier between the water and the infusate is breached for some reason. The use of a warm water bath as the heat transfer mechanism requires continuous maintenance to keep the water clean and the pumping system operating with sufficient capacity. Air transported from infusate bags and bubbles generated from the infusate are collected and separated by the gas elimination device, and air is eliminated through a port in the device. At times, a large mass of collected bubbles can block the port, thereby preventing air from being vented. Then, the collected bubbles will cause detection of air that is not quickly vented, and the clamp will be activated. In such a case, the system can be restarted only after clearing or replacing the gas elimination device. In this known system, set up preceding each use requires separate handling and installation of the heat exchanger, the gas elimination device, and the length of patient line that is led through the clamp.

There is a need for a heat exchanger for high flow rate infusion that effectively transfers heat to a rapidly-flowing infusate without risk of contaminant exchange between the infusate and a heat transfer fluid. Another desirable advance would reliably eliminate air from the infusate without blocking an air vent. System set up would be improved by reduction of the number of devices required to be installed each time the system is used.

SUMMARY

A heat exchanger to conductively heat infusate flowing therethrough at a high flow rate includes a laminar flow path and a bubble trap in fluid communication with the laminar flow path.

A heat exchanger has a laminar fluid flow path receivable between the heating plates of a high flow rate infusion unit to which heat is conducted by contact with the heating plates. A bubble trap and a valve are integrated with the heat exchanger. The bubble trap collects air from the infusate exiting the laminar flow path, and includes an air vent in contact with the infusate that vents the air from the bubble trap. The valve shuts off the flow of infusate if air is detected in the bubble trap.

A heat exchanger embodiment constituted of a flat, elongate warming cassette with a fluid container defining a laminar fluid flow path is slidable in a heating unit between a seated position where the fluid container is in heat-transferring contact with heating plates and an extracted position outside of the electrical heating unit. The warming cassette includes a housing attached to the fluid container. The housing contains a bubble trap and a valve. The bubble trap is disposed in fluid communication with the laminar flow path to collect air from infusate flowing out of the fluid path. The bubble trap includes an air vent in contact with the infusate that vents air from the bubble trap. The valve, disposed in fluid communication with the bubble trap, has an open state permitting infusate to flow out of the warming cassette and a closed state blocking infusate from flowing out of the warming cassette.

The bubble trap includes a flow expansion chamber to collect large bubbles, a recirculation chamber to collect large to medium bubbles, a laminar flow chamber where air is released and detected, and an outlet chamber where the infusate exits the heat exchanger.

The heat exchanger is constructed for sensing the presence and level of air in infusate flowing through the bubble trap in order to control the flow of infusate out of the bubble trap in response to detected levels of air. Preferably, the infusion unit controls the state of the valve in response to detected levels of air in order to permit or prevent infusate to flow.

The unification of a laminar flow path, bubble trap, and shut off valve in an integrated heat exchanger construction yields a single, easily handled appliance that simplifies setup and operation of infusate warming, bubble management, air elimination, and safety shut off for high flow rate infusion.

BRIEF DESCRIPTION OF THE DRAWINGS

FIG. 5 is an exploded view of a warming cassette, in perspective.

FIG. 8 is an exploded top view of the electrical heating unit with the warming cassette in the seated position between the heating plates.

FIG. 9 is a sectional view of the electrical heating unit taken along line 9-9 of FIG. 7 with the warming cassette in the seated position between the heating plates.

DETAILED DESCRIPTION

In this detailed description, a heat exchanger including a laminar flow path for a high flow rate infusion unit is described. A high flow rate is a flow of infusate through a patient line at a rate that is sufficient to administer a large amount of infusate quickly to a person. For example, a high flow rate infusion system may administer blood to a trauma patient at a rate of 30 liters per hour (30 L/hr), or higher, measured through a line connected intravenously to the patient (a "patient line"). A "laminar flow path" is a thin, relatively flat, non-sinuous space through which a sheet of infusate can flow from an inlet port to an outlet port.

The novel designs and embodiments to be described provide a number of benefits with respect to previously known high flow rate infusion systems. Infusate is heated by direct contact between the heat generating mechanism and a heat exchanger, thereby eliminating an intermediary medium (such as water) to transport heat from a heater to the heat exchanger. This mode of heat transfer may be referred to as "dry heat" because it does not use water, or another fluid. An exemplary heat exchanger construction unifies a unidirectional, laminar flow path where infusate is heated, a bubble trap that continually vents air from the infusate, and a valve to regulate infusate flow. Bubbles are separated and collected from infusate and air is eliminated through a vent in contact with the infusate, which reduces shut downs caused by build up of bubbles, thereby ensuring uninterrupted infusate flow for longer periods of time than the previously known high flow rate infusion systems. The unified construction of the heat exchanger yields a single, easily handled appliance that simplifies setup and operation of heat exchange, air elimination, bubble entrapment, and safety shut off for a high flow rate infusion unit.

High Flow Rate Infusion System

Figure 1:
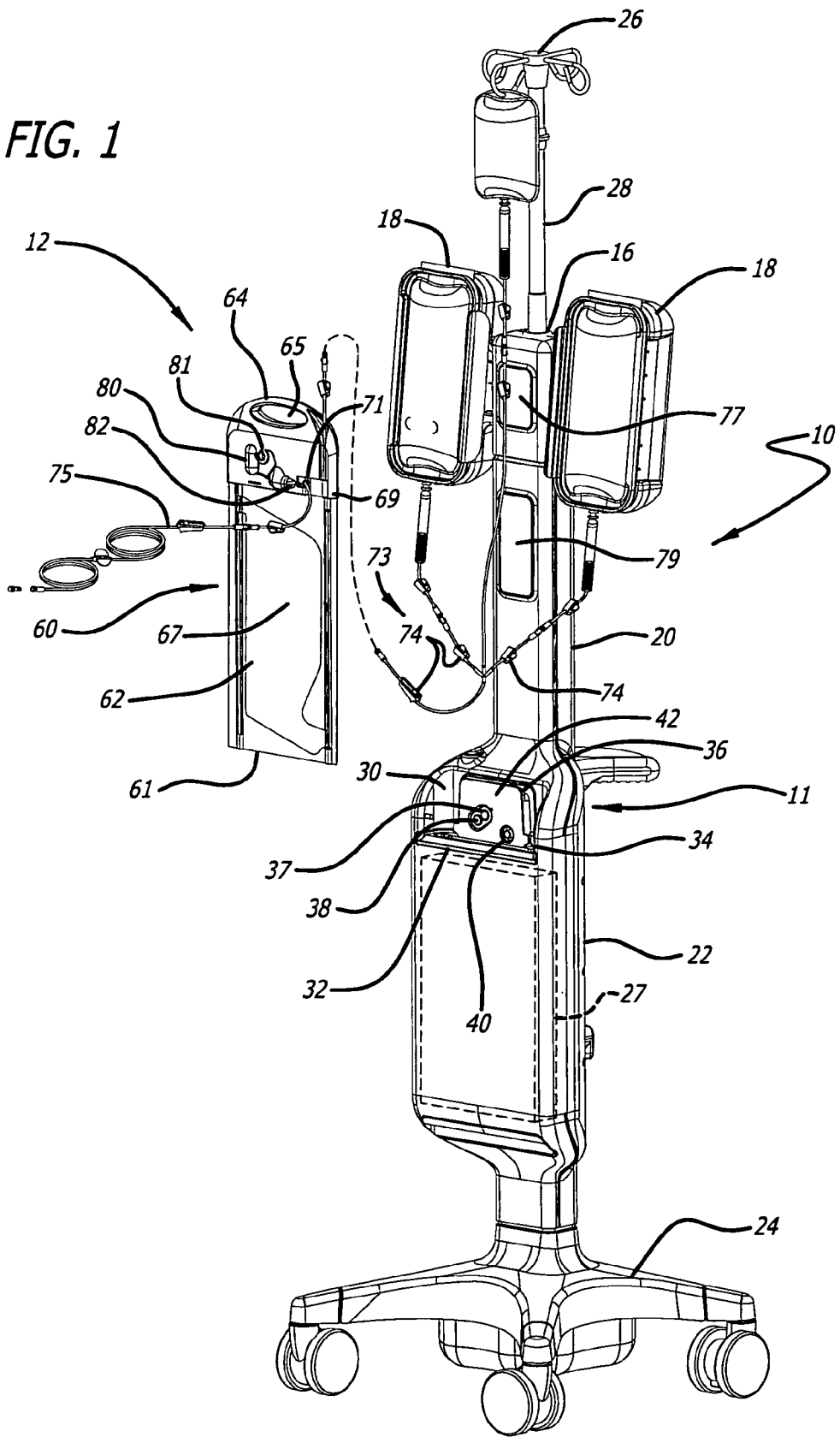
FIG. 1 is a perspective view of a high flow rate infusion unit and a heat exchanger in an extracted position with respect to the infusion unit.
Figure 2:
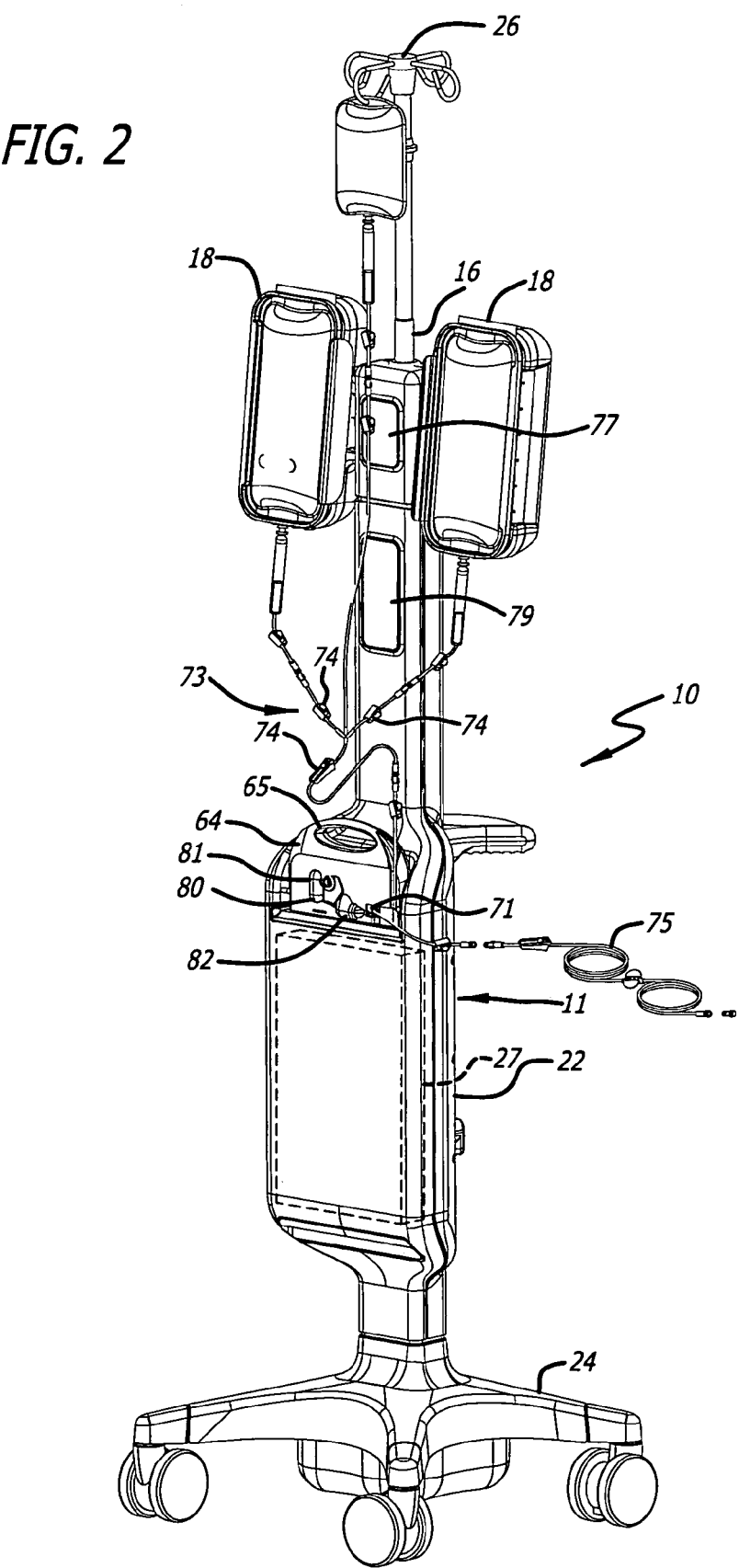
FIG. 2 is a perspective view of the high flow rate infusion unit with the heat exchanger in a seated position with respect to the infusion unit.

Refer now to FIGS. 1 and 2 which illustrate a high flow rate infusion system including a high flow rate infusion unit 10 and a heat exchanger 12. The infusion unit 10 has a kiosk or tower construction with a casing including an upper section 16 with dual, pressure-actuated infusers 18, a neck 20 extending from the upper section 16, and a pedestal 22 supporting the neck 20. Preferably, a wheeled support base 24 allows the infusion unit 10 to be easily moved or repositioned on a floor or other surface. A rack 26 is supported above the upper section 16 by a shaft 28 slidably retained in the upper section 16. Bags of infusate may be hung on the rack 26 as shown. The longitudinal axis of the infusion unit 10 is generally perpendicular to the surface on which it is supported. Electronics for operating the infusion unit 10 are contained in the neck 20. A heating unit 27 constituted of resistively-heated plates is contained within the pedestal 22. Sensors, actuators, and a pneumatic system for delivering pressurized air are distributed as needed between the neck 20 and the pedestal 22. The pedestal 22 has a recessed surface portion 30 where a bezel 32 is mounted. The bezel 32 has an elongate opening or slot 34. As seen in FIG. 1, a mounting block 36 in the recessed surface portion 30 is disposed along one side of, and perpendicularly to, the bezel 32. Sensors 37 and 38 are mounted to and extend through the body of the mounting block 36 to a major surface 42 thereof. A valve actuator 40 (best seen in FIG. 12B) mounted to a rear surface of the mounting block 36 includes a piston 41 that operates through the major surface 42.

The construction of the heat exchanger 12 includes a laminar flow path through which a broad sheet of infusate flows. In use, when the heat exchanger 12 is installed in the infusion unit 10, the laminar flow path of the heat exchanger is sandwiched between a pair of electrically-operated heating plates, such that each side of the laminar flow path is in close heat-conducting contact with a respective one of the pair of heating plates. When the heating plates are operated, heat exchanged between the plates and the laminar flow path warms the infusate as it moves through the laminar flow path. With reference to FIGS. 1 and 2, an exemplary construction of the heat exchanger 12 is illustrated. Preferably, the heat exchanger 12 may be constructed as an elongate, quadrilateral, generally flat or laminar warming cassette 60. The cassette 60 includes a distal end 61, a fluid container 62, and a housing 64 with a hand grip 65. The fluid container 62 defines a laminar flow path 67 of the warming cassette 60. The cassette 60 includes an input port 69 and an output port 71, each in fluid communication with the laminar flow path 67. When viewed end on looking toward the distal end 61, the cassette has a thin, but relatively elongate aspect so as to be slidably inserted into the slot 34 in the bezel 32 with the fluid container sandwiched between and in heat-conducting contact with the heating plates, and slidably extracted therefrom.

In FIG. 1, the cassette 60 is shown extracted from the infusion unit 10; in FIG. 2, the cassette 60 has been inserted in the infusion unit 10, distal end 61 first, through the slot 34 into the electrical heating unit 27, where the fluid container is disposed between and in contact with the heating plates. Preferably, when the cassette 60 is inserted into the slot 34, the longitudinal axis of the infusion unit 10 and a major axis of the cassette 60 are generally aligned and parallel. Thus, when the cassette is received in the slot 34, it is oriented to be disposed substantially vertically with respect to a surface supporting the infusion unit 10. The cassette 60 is removed from the infusion unit 10 by grasping the hand grip 65 and pulling the cassette upwardly, out of the slot 34. In most aspects, after infusion of a patient, a used cassette 60 is extracted from the infusion unit 10 and processed for medically safe disposal. A new, unused cassette 60 is inserted into the infusion unit 10 prior to commencing infusion of another patient.

With further reference to FIGS. 1 and 2, the infusion unit 10 is prepared for operation by placing a bag containing infusate into either or both pressure infusers 18, inserting the cassette 60 into the slot 34, and connecting the bag or bags to the cassette 60 by IV tubing. An IV tube set such as the Y tube set 73 is connected to each bag and to the input port 69 of the cassette 60. The Y tube set 73 is conventional and includes manually-operated means 74 in each branch of the Y connected to a bag to pinch off the branch when the bag connected to it is not used. An IV tube 75 is connected to the output port 71 of the cassette 60 and is connected by known intravenous means to a patient. The IV tube 75 constitutes the "patient line" through which a flow of warmed infusate is delivered intravenously to a patient at a rate that is sufficient to administer a large amount of infusate quickly to the patient. For example, the rate may be 30 L/hr, or higher. The infusion unit 10 is then activated by means of controls operated by a user using control panel 77. ON/OFF control is afforded by way of control panel 79.

With further reference to FIGS. 1 and 2, when activation of the high flow rate infusion unit 10 occurs, electrical power is applied to resistively heat the heating plates and pressurized air is introduced into an inflatable bladder in a pressure infuser 18. As the bladder 103 inflates, it presses against the fluid-filled bag in the pressure infuser 18, which forces the fluid into the IV tubing set 73. The pressure against the bag is transferred to the fluid, forcing it to flow to and through the cassette 60 at a rate higher than that which would result if it were flowing in response to gravity only. The infusate flows into the cassette 60 through the input port 69 and therethrough into the laminar flow path 67 near the distal end 61. The infusate fans out into a thin laminar sheet and flows through the laminar flow path 67, expanding the fluid container 62 so that it contacts and presses against the heating plates. The infusate continuously absorbs heat from the heating plates as it flows. As the infusate approaches the housing 64, the shape of the laminar fluid flow path 67 concentrates the warmed infusate into a narrow, high speed stream that flows into the housing 64, through a bubble trap 80 where bubbles are separated and collected from the stream of infusate, and where air is vented through an air vent 81. Passing through the bubble trap 80, the narrow, high speed stream of warmed infusate flows through a valve 82, out the output port 71, into the patient line 75, through which it is administered intravenously to a patient.

Figure 3:
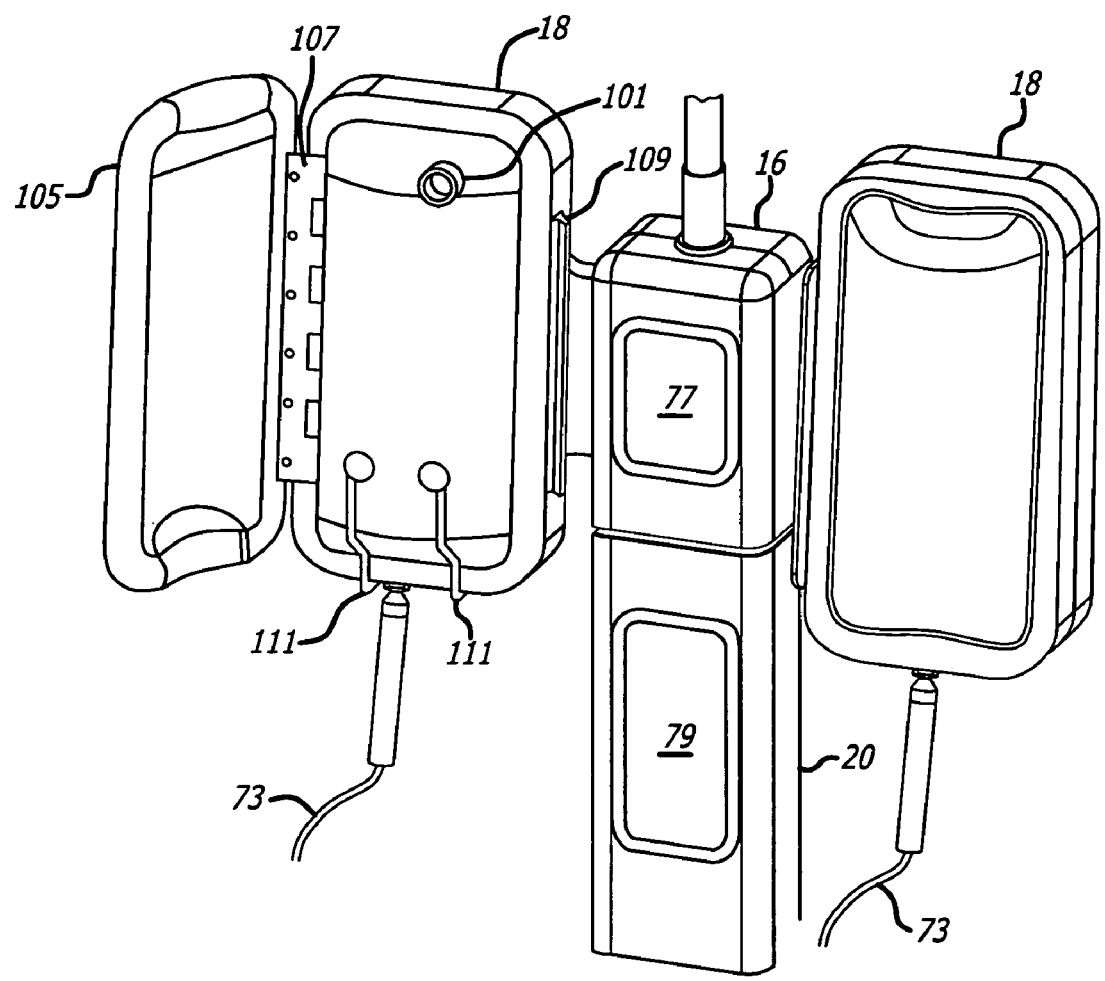
FIG. 3 is an enlarged perspective view of the top of the high flow rate infusion unit with two pressure-actuated infusers, in which one pressure infuser is opened to receive an intravenous (IV) bag.
Figure 4B:
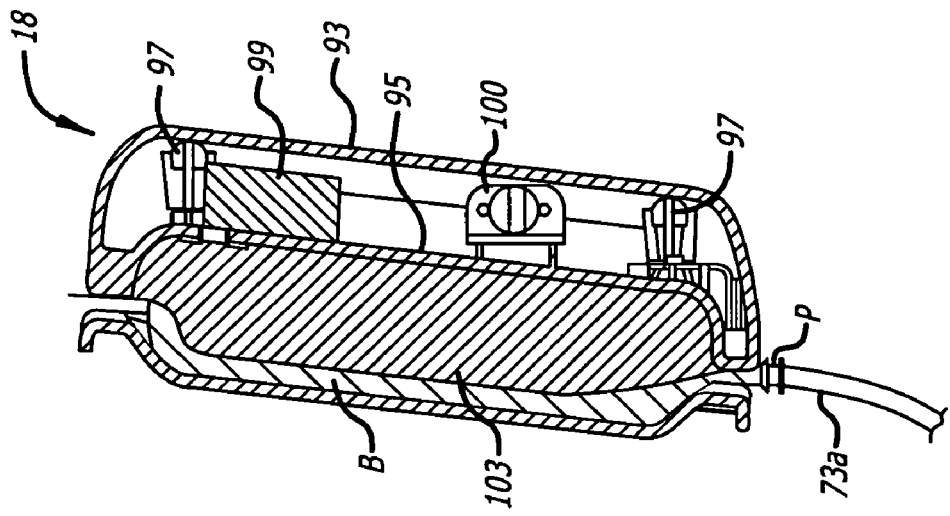
FIG. 4B is a side sectional view of the pressure infuser of FIG. 4A with the IV bag empty and the bladder inflated.
Figure 4A:
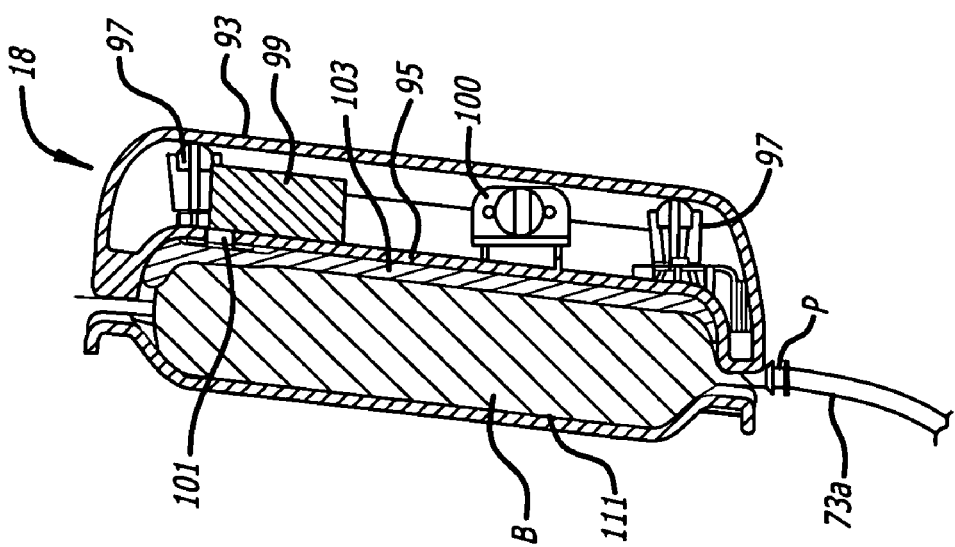
FIG. 4A is a side sectional view of a pressure infuser with a full IV bag mounted therein against a deflated bladder.

With reference to FIGS. 3, 4A, and 4B, each pressure infuser 18 is constructed to receive a full bag of infusate and to expel the infusate from the bag at a high rate of flow. Each pressure infuser 18 has a body constituted of a rear shell 93 and an inner shell 95 fixed to the rear shell 93 and supported thereagainst by spacers 97. In the space between the shells 93 and 95, a pneumatically controlled valve 99 and an electronically controlled, three way pneumatic valve 100 are mounted to the rear surface of the inner shell 95. A port 101 extending through the inner shell 95 connects the valve 99 to an inflatable bladder 103 supported on the front surface of the inner shell 95. Each pressure infuser 18 has a door 105 that swings on a hinge 107 mounted to the body of the pressure infuser 18. Each door 105 is held shut by an elongate releasable latch 109 mounted to the body of a pressure infuser 18. A pair of spring retainers 111 is mounted to the body of each pressure infuser 18 so as to extend into the space between a door and an inner shell. The springs support bags when the doors open and aid door opening.

With further reference to FIGS. 3 and 4A, the door 105 of a pressure infuser 18 is opened, and a full bag B of infusate with a lower port P is placed in the pressure infuser 18, such that the port P extends downwardly through a gap between the door 105 and the body of the pressure infuser 18. The bag B is retained against the front surface of the inner shell 95 by the pair of spring retainers 111 and by closing and latching the door 105. Preferably, the bag B has a construction that is conventional for IV bags, although the design may be customized to accommodate other design requirements. For a conventional construction, the bag B is connected to one line of the Y tube set 73 by a spike on the end of the line that penetrates the bottom of the bag B through the port P. With reference to FIGS. 4A and 4B, infusate is pressurized and forced from the bag B, through the port P, when the bladder 103 is inflated by pressurized air provided by the two-way valve 99 through the port 101. Pressurized infusate flows out of the bag B through the port P into the fine 73a, and therethrough to the heat exchanger 12. When the bag B is emptied, the setting of the valve 99 is reversed, and the bladder 103 is deflated by venting air from the bladder through the port 101. The empty bag B may then be removed from the pressure infuser 18 and replaced by another full bag.

The flow rate of the infusion system just described is established by, among other parameters, the viscosity of the infusate, the pressure capacity of the pressure infusers 18, and the resistance to fluid flow. Infusate viscosity varies according to the nature of the fluid being infused. The rate of inflation of the bladders 103 and the relative sizes of the bladders 103 and infusate bags are the principal determinants of pressure capacity. The broad laminar flow path in the fluid container 62 reduces flow resistance, compared to previous heat exchanger designs based on a flat cassette, by elimination of curves, bends, and abrupt changes in flow direction. Tubing can be selected to provide a range of flow resistance appropriate to the other factors and the desired flow rate. Preferably, the high flow rate infusion system of FIGS. 1 and 2 administers blood to a trauma patient at a rate of 30 liters per hour (30 L/hr), or higher, when the pressure infusers 18 are operated to pump infusate by inflation of the bladders 103. Of course, the infusate bags may be connected to a heat exchanger 12 installed in the infusion unit 10 for flow of infusate through the infusion system at a lower pressure. In fact, infusate will flow without activating the pumping operation of the pressure infusers 18 at all, in which case, infusate will flow through the system by gravity. Thus, the infusion system of FIGS. 1 and 2 can provide warmed infusate at flow rates in the range of from 0 to at least 30 L/hr; in some instances, the infusion system can provide warmed infusate at a maximum flow rate exceeding 70 L/hr.

Heat Exchanger

Figure 6:
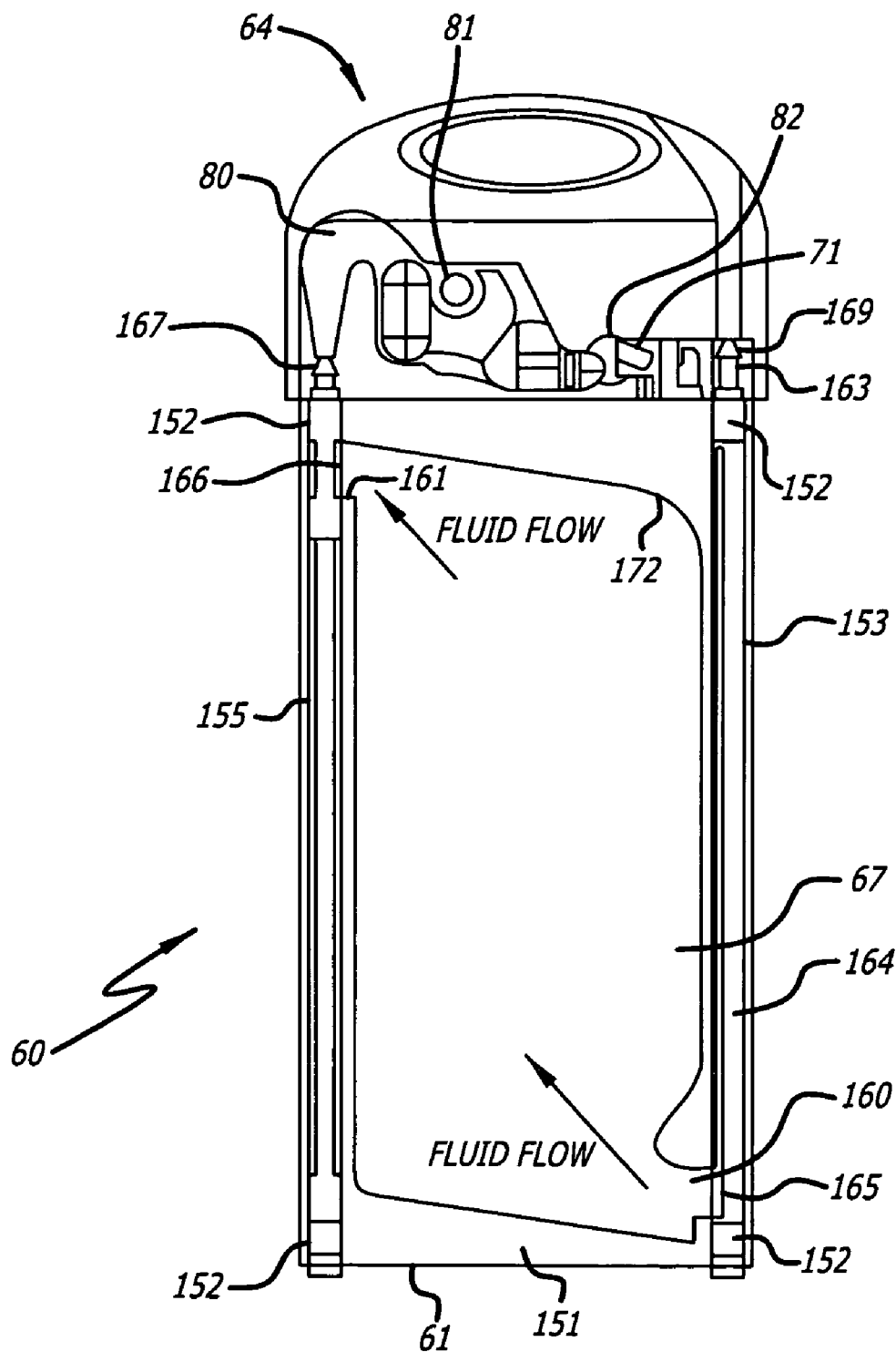
FIG. 6 is a plan view of the assembled warming cassette.

Infusate expelled from a pressure-activated infusate bag travels at a high flow rate through tubing connecting the bag to the heat exchanger in which it is warmed for administration to a patient. The heat exchanger is exemplified by a warming cassette construction adapted for use in the infusion unit 10 of FIG. 1. In this description of the warming cassette, the term "heat exchanger" is used to denote the warming cassette, even though heat exchange occurs through the fluid container and is only one function of the warming cassette. The warming cassette 60 has an integrated construction that unites a heat exchanger in the form of the fluid container 62, with a bubble trap and shut-off valve disposed in the housing 64. This construction enables the heat exchanger, bubble trap, and shut-off valve to be installed in and removed from the infusion unit 10 in a single step. With reference to FIGS. 5 and 6, the fluid container 62 is a thin, quadrilaterally-shaped, fluid-tight pouch 150 formed by joining coextensive sheets of flexible plastic material together by a pattern of fluid-resistant seals 151 around the periphery of the pouch 150. Two semi-rigid plastic rails 153 and 155 are positioned between the coextensive sheets and between elements of the seals 151 just inside of and parallel to the elongate edges 157 of the pouch 150. The rails 153 and 155 are sealed to the sheets of flexible plastic material by fluid-resistant seals 152, near the ends of the rails. The laminar flow path 67 is positioned between the rails 153 and 155 and has an inlet 160 and an outlet 161. The rail 153 has a straw like construction with a central passageway 162 that opens through one end 163 of the rail 153 and extends to a groove 164 terminated in a short longitudinal slot 165 near the opposing end. The slot 165 opens through the side surface of the rail into the inlet 160 to laminar fluid flow path 67. The rail 155 has a short central passageway 162 that opens into the outlet 161 through a short longitudinal slot 166 and runs from there to and through one end 167 of the rail 155. Preferably, the housing 64 is formed by molding plastic to yield two rigid complementarily-shaped pieces that are joined together over ends 163 and 167 of the rails 153 and 155 and the near short edge 168 of the pouch 150. Together, the housing 64 and the rails 153, 155 form a generally quadrilateral frame on which the pouch 150 is supported.

Many materials and processes may be used to construct the warming cassette 60. For example, with reference to FIGS. 5 and 6, we assemble the fluid container 62 from sheets of laminated material which include a layer of polyethylene material on a layer of polyester; we use rails made of molded polyethylene; and we assemble the housing 64 using pieces made of a molded acrylic, polycarbonate, or blended medical grade plastic such as Cyrolite®. The sheets are oriented with the polyethylene layers facing and the rails are disposed between the polyethylene layers in the orientations seen in FIGS. 5 and 6. The seals 151 and 152 in this case may be formed by heat applied through the polyester layers. Because of difficulty in sealing the polyethylene rails to the polycarbonate housing, we use compliant sleeves 169 and 170 made of polyvinyl chloride (PVC) to attach the ends 163 and 167 of the rails 153 and 155 to the housing. In this regard, the sleeves 169 and 170 are contained within the housing 64 and their outside surfaces are sealed with solvent to complementary structures in the housing. Barbs formed on the ends 163 and 167 of the rails 153 and 155 mechanically seat against the interior surfaces of the sleeves 169 and 170, attaching the rails 153 and 155 to the housing 64 in the positions shown in FIG. 6.

Infusate flow through the warming cassette 60 is shown in FIG. 6. The end 163 acts as the input port 69 of the warming cassette 60. Infusate enters the warming cassette through a tube (not shown) in fluid communication with the end 163, flows through the central passageway 162 in the rail 153 and exits the rail 153 through the slot 165. Infusate flows through the inlet 160 wherefrom it fans out into a broad thin sheet that extends across the laminar flow path 67 that flows toward the housing 64. As the sheet of infusate approaches the housing 64, it is funneled toward the outlet 161 by the curve 172 formed by the contour of the seal 151. The infusate flows out of the laminar flow path 67 through the outlet 161 into the short passageway of the rail 155 via the slot 166. The infusate flows out of the short passageway of the rail 155 through the end 167 and into the bubble trap 80 in the housing 64 of the warming cassette 60. The infusate flows through the bubble trap 80 and the valve 82, to and out of the output port 71.

Heating Unit

Figure 7:
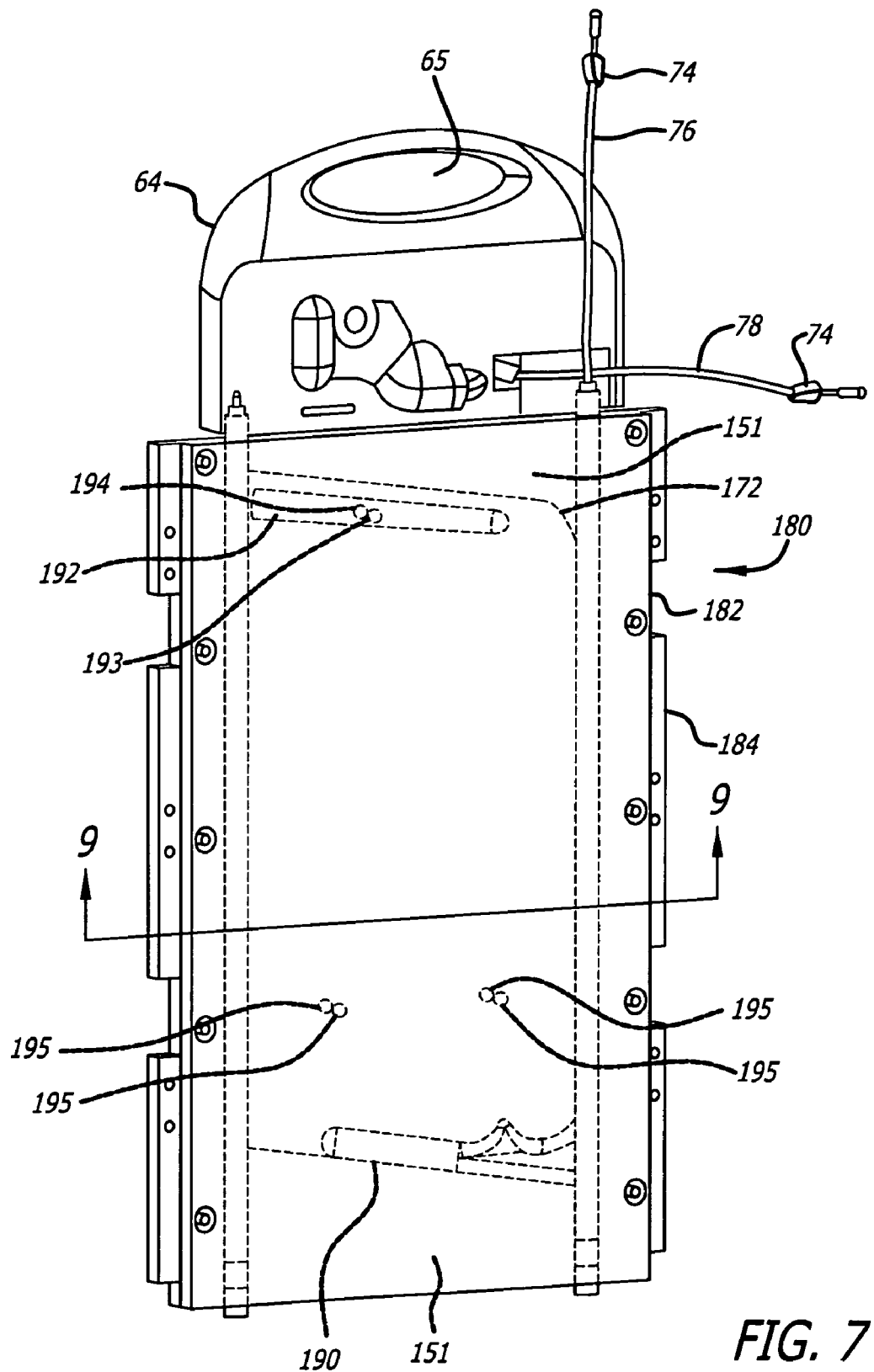
FIG. 7 is a side elevation view of an electrical heating unit of the high flow rate infusion unit with the warming cassette in the seated position with respect to heating plates of the electrical heating unit.
Figure 20:
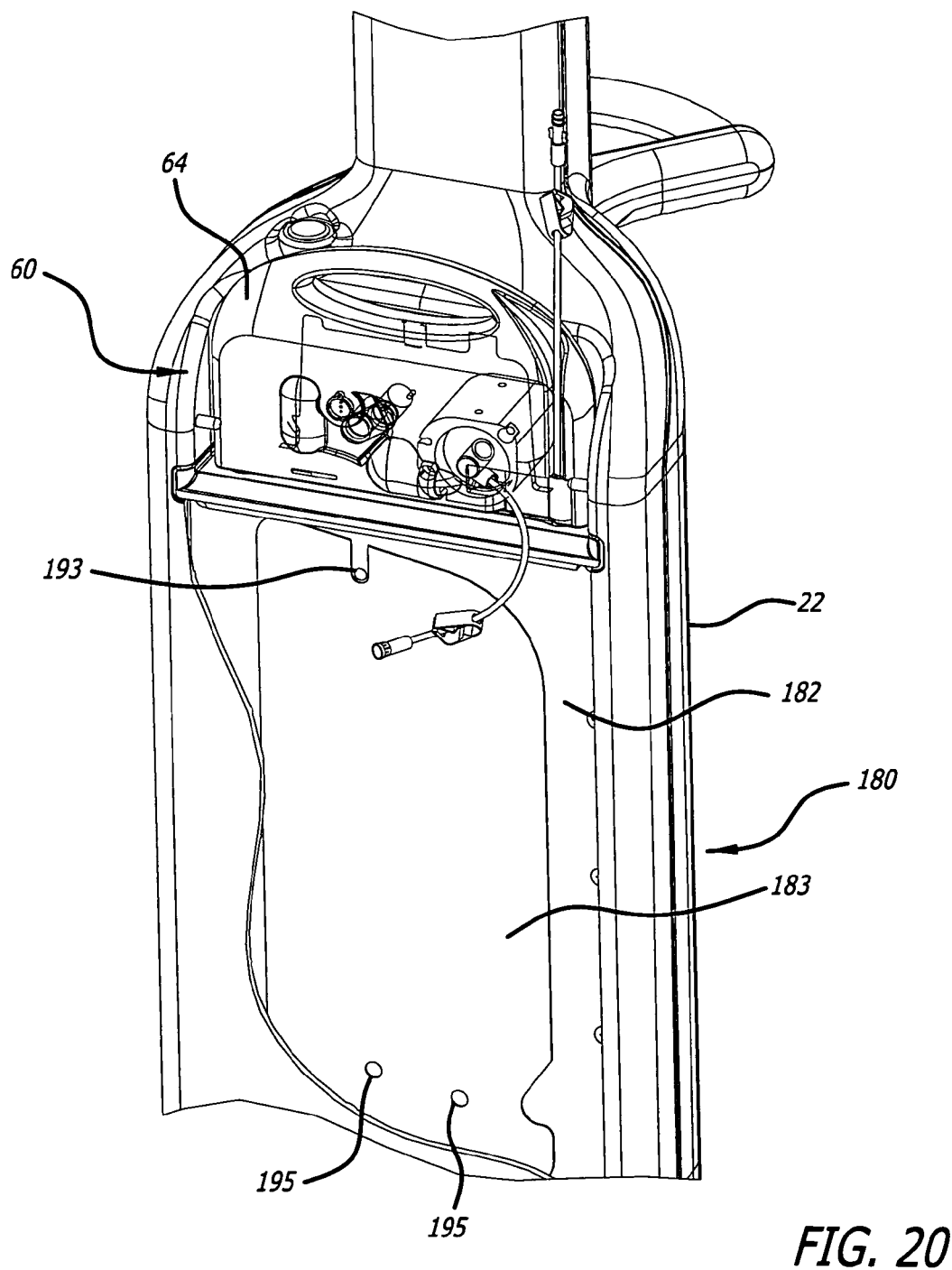
FIG. 20 is an enlarged perspective view, partially cut away, of the front of the high flow rate infusion unit with the warming cassette seated in a heating unit thereof.

With reference now to FIGS. 7, 8, 20, and 21, the warming cassette 60 is shown inserted into a heating unit 180 supported in the infusion unit 10. The heating unit 180 includes two opposed heating plates 182 and 184 that define a narrow laminar space within which the fluid container 62 is seated. Preferably, the heating plates 182 and 184 are formed of low thermal resistance aluminum anodized with a hard coat. The heating plates 182 and 184 conduct heat generated by a pair of resistance heaters on the outside surfaces of the heating plates. One such heater 183 is best seen in FIG. 20. The resistance heaters 183 may comprise, for example, laminated silicone resistance heaters, or equivalents thereof. The heating plates 182 and 184, with the heaters 183 mounted to the outside surfaces thereof, are conventionally mounted in the pedestal 22 of the infusion unit 10. As seen in FIGS. 7-9, the heating plate 182 has elongate parallel grooves 186 near its lateral edges which face opposing elongate parallel grooves 188 in the heating plate 184. As best seen in FIGS. 8 and 9, the facing grooves 186, 188 form elongate parallel channels that accommodate the rails 153 and 155 and guide the warming cassette 60 to and from correct seating as it slides between the heating plates 182 and 184. As seen in FIGS. 8 and 9, the warming cassette 60 has a thin, but relatively elongate aspect (when viewed distal end on) so as to be slidably inserted through the slot 34 in the bezel 32 with the fluid container 62 sandwiched between and in heat-conducting contact with the heating plates 182 and 184, and slidably extracted therefrom. As seen in FIG. 9, the laminar flow path 67 is sandwiched between and in close abutting contact with the heating plates 182 and 184 when the warming cassette 60 is installed in the infusing unit 10, thereby eliminating the need for an intermediary medium to transport heat to the warming cassette 60.

In FIG. 7, a pair of opposing shallow transverse channels 190 formed in the surfaces of the heating plates that face the fluid container 62 run from an edge of the heating plate surface. Corresponding ends of the channels are near the location of the slot 165 in the rail 153 when the cassette 60 is seated in the electrical heating unit 180. The pressure of infusate flowing out of the slot 165 forces opposing strips of the fluid container 62 into conformance with the channels 190, thereby forming an input manifold through which infusate can spread into the laminar flow path 67. Similarly, a pair of opposing shallow transverse channels 192 formed in the surfaces of the heating plates that face the fluid container 62 cause the formation of an output manifold in the fluid container 62 that channels infusate out of the laminar flow path 67 into the slot 166 in the rail 155.

FIG. 7 also shows monitoring and extraction elements of the heating plates 182 and 184. A pair of opposing through holes 193 and 194 are formed in the heating plates 182 and 184 for positioning heat sensors (not seen) in the pair of opposing shallow transverse channels 192 that cause the formation of an input manifold in the fluid container 62. At these opposing locations, the temperature of infusate flowing out of the warming cassette may be measured. Two pairs of opposing through holes 195 are formed in the heating plates 182 and 184 for channeling jets of pressurized air against the sides of the fluid cassette in order to dislodge the warming cassette from the heating plates 182 and 184. In this regard, when the flow of infusate ceases, a sheet of infusate fills the fluid container 62, pressing the sides of the fluid container against the opposing surfaces of the heating plates 182 and 184. Surface tension and friction between the fluid container 62 and heating plates 182 and 184 can make it difficult to dislodge warming cassette 60. Jets of pressurized air through the holes 195 force infusate out of the fluid container 62, thereby breaking the surface tension and reducing the friction, making it easier to extract the warming cassette 60.

With reference to FIGS. 6 and 9, important benefits of the warming cassette construction will be appreciated. The dry heat mode of warming infusate shown in these figures eliminates the need for a fluid such as water to transport heat to the infusate. At the same time, the broad, unidirectional laminar flow through the heat exchanger that is constrained between the heating plates minimizes flow path resistance by eliminating successive curves and reverses in the direction of flow. Presuming a maximum width of the laminar flow path that is dictated by design constraints, it is, of course, possible to reduce flow resistance further by increasing the spacing between the heating plates, but this also reduces the rate of heat transfer from the heating plates to the infusate. Thus, there are optimal balances between fluid flow and heat transfer that can be achieved for various applications of the warming cassette construction illustrated and described above.

Bubble Trap and Shut Off Valve

Figure 10:
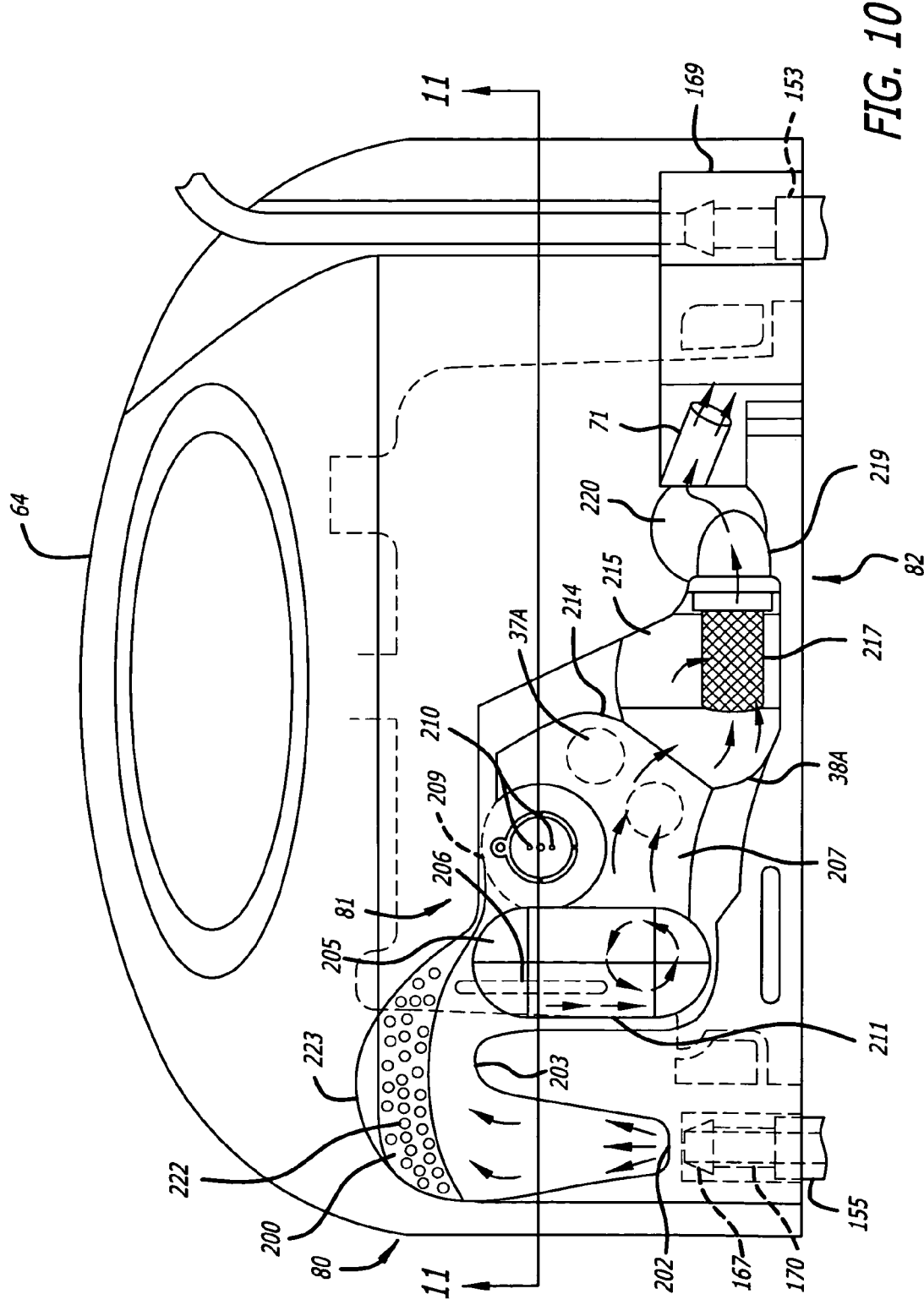
FIG. 10 is an enlarged view of the front face of a housing of the warming cassette of FIG. 6 showing a bubble trap, sensor couplers, and a valve.
Figure 12A:
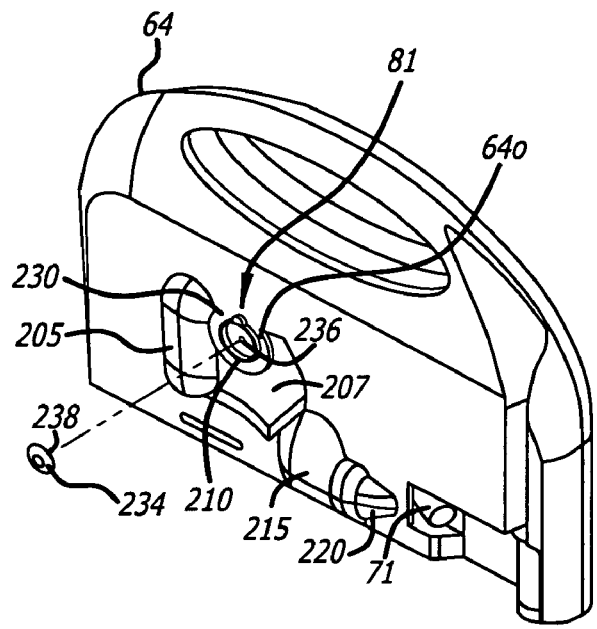
FIG. 12A is a perspective view of the front face of the housing of FIG. 10, partially disassembled.
Figure 12B:
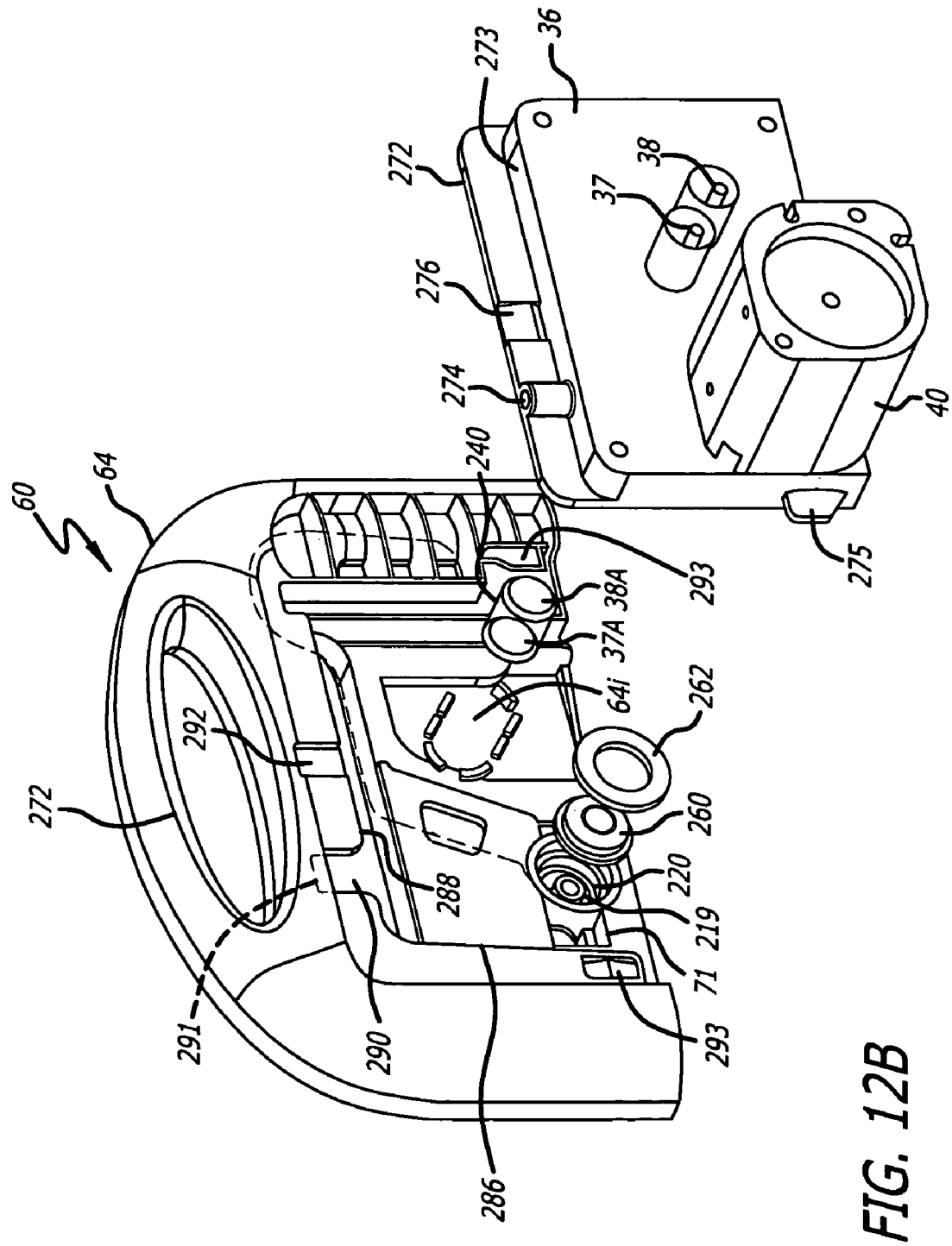
FIG. 12B is a perspective view of the back face of the housing of FIG. 10, partially disassembled and shown with respect to a mounting flange in the high flow rate infusion unit with sensors and an actuator partially disassembled therefrom.

For the purposes of the following explanation, the housing 64 has a front face, seen in FIGS. 10 and 12A, that is visible to an operator when the warming cassette 60 is installed in the infusion unit 10, and a rear face, seen in FIG. 12B that faces the mounting block 36 when the warming cassette 60 is installed in the infusion unit 10. With reference to FIG. 10, after infusate has been warmed in the heat exchanger, the bubble trap 80 separates and collects air and bubbles from the infusate as it streams in a flow path (a "trap flow path") through the bubble trap 80, and vents air through a vent. If a threshold level of air is detected in the bubble trap 80, the valve 82 closes, thereby stopping the flow of warmed infusate to the patient line. Preferably, the bubble trap 80 and valve 82 are integral parts of the housing 64. That is to say, the molding process with which the components of the housing 64 is made forms the structural components of the bubble trap 80 and valve 82 in the housing components, so that the components of the bubble trap 80 are assembled and contained within the housing 64 when the molded halves of the housing are joined. This construction is preferred, but should not be limiting. For example, a bubble trap can be constructed separately and placed within the housing 64 as the housing is assembled.

The bubble trap 80 includes a trap flow path designed for high flow rates, that is, flow rates of 30 L/hr, and higher. Preferably, the bubble trap operates with fluid flow rates in the range from 0 to 70 L/hr, or higher, through the trap flow path. The trap flow path is constructed to separate bubbles from the infusate in a succession of stages. The stages include, in sequence, a flow velocity reduction chamber ("reduction chamber"), a separation chamber, a laminar flow chamber, and an outlet chamber.

Figure 11:
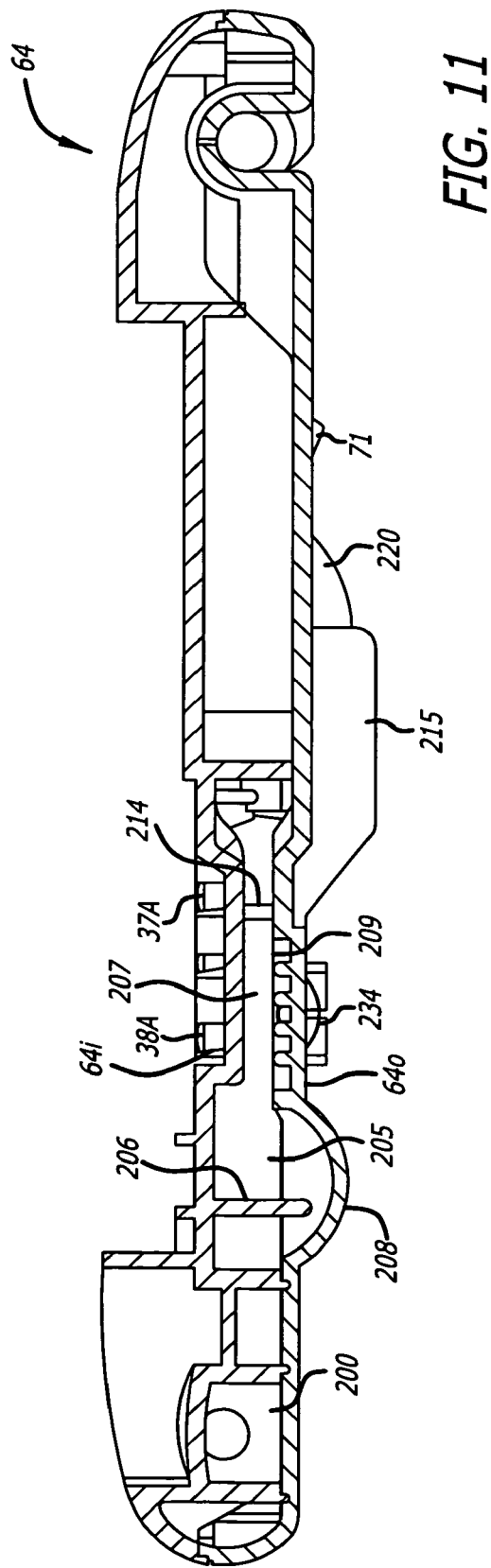
FIG. 11 is sectional view of the housing of FIG. 10 taken along line 11-11 of FIG. 10.
Figure 13:
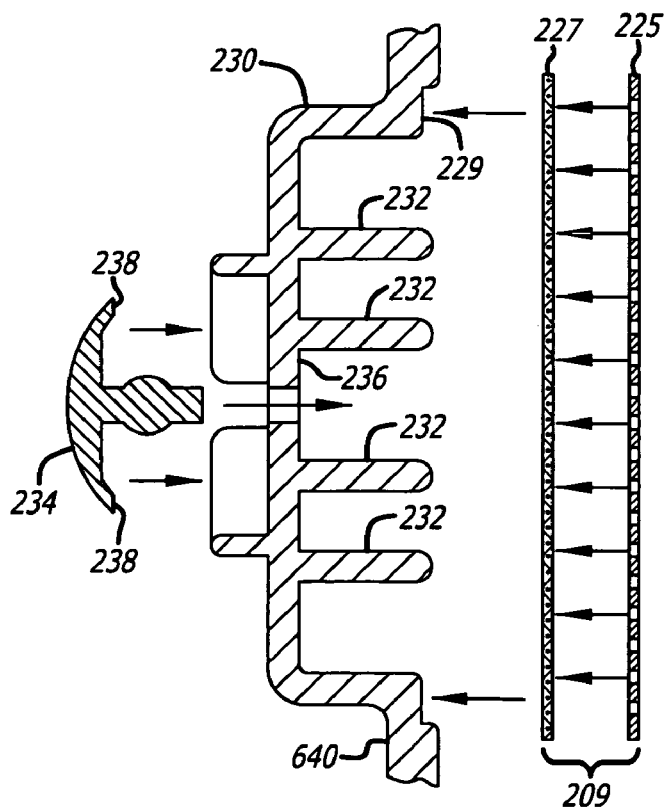
FIG. 13 is an enlarged sectional view showing details of an air vent.
Figure 16:
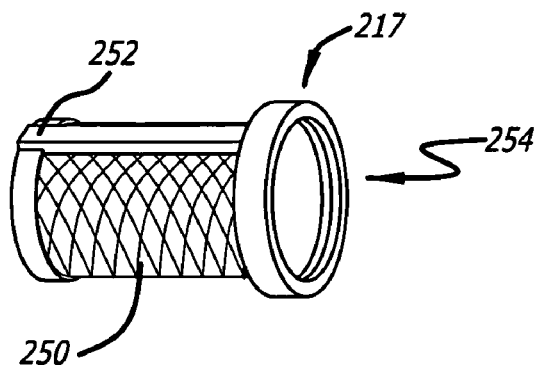
FIG. 16 is an enlarged perspective view of a bubble trap hydrophilic screen.

With reference to FIG. 10, the reduction chamber 200 is in fluid communication with the central passageway of the rail 155, so that infusate flows out of the end 167 of the rail 155 into the reduction chamber 200. The reduction chamber 200 has a hook-shaped cross section that increases in width from the end 202 to the top portion of the hook. When the warming cassette is oriented vertically in the infusion unit 10 as shown in FIG. 2, the end 202 is in the bottom of the bubble trap 80. In this case, the top portion of the hook bends downwardly at 203 to the separation chamber 205. In some aspects, a baffle 206 may be provided to channel infusate flow into the separation chamber 205. With reference to FIGS. 10 and 11, the trap flow path narrows substantially in the transition from the separation chamber 205 to the laminar flow chamber 207. As best seen in FIG. 11, the laminar flow chamber 207 has a narrow cross section with an outer side 64o in the front face of the casing 64 and an opposing inner side 64i in the rear face of the casing 64. Referring to FIGS. 10, 13, and 16, a disc-shaped hydrophobic membrane 209 is welded to the inside surface of the outer side 64o, spaced apart from apertures 210 through the outer side 64o. When infusate flows through the bubble trap, the hydrophobic membrane 209 is continually in contact with the infusate as it flows through the laminar flow chamber 207. Advantageously, the accelerated flow of infusate through the laminar flow chamber keeps bubbles from sticking to the surface of, and clogging, the hydrophobic membrane 209. As best seen in FIGS. 10 and 12B, first and second sensor couplers 37A and 38A are supported on the outside surface of the inner side 64i. Presume that the warming cassette 60 is oriented vertically in the infusion unit 10 as shown in FIG. 2. In this case, as shown in FIG. 10, the hydrophobic membrane 209 is positioned above and upstream of both sensor couplers 37A and 38A, and the first sensor coupler 37A is positioned above the second sensor coupler 38A. As seen in FIGS. 10 and 11, the trap flow path transitions at 214 to the outlet chamber 215. As best seen in FIG. 10, infusate flows out of the outlet chamber 215 through a thimble-shaped hydrophilic screen 217 into a short riser 219 by which it enters one side of a circular valve chamber 220 that is in fluid communication with the output port 71. Preferably, the outlet chamber 215 is widened with respect to the laminar flow path in order to reduce flow velocity of the infusate through the hydrophilic screen 217 so that bubbles will not be pushed through the screen and can rise up off to the air pocket forming in the top portions of the bubble trap 80.

In some instances, the housing 64 may be transparent in order to enable an operator to see and judge bubble trap operation through the separation chamber 205; in these instances, as best seen in FIG. 11, the housing 64 may bulge outwardly at 208 thereby to enable the operator to clearly see the infusate level in the bubble trap 80. For example, the operator may view the cascade of infusate flowing over the bend 203 to visually ascertain infusate flow and judge the flow rate.

With reference to FIG. 10, infusate flows into the bubble trap 80 from the end 202 of the reduction chamber 200. Presume that the warming cassette is oriented vertically in the infusion unit 10 as shown in FIG. 2. In this case, as the bubble trap 80 is primed with infusate through the end 202, the infusate wells up from the bottom of the bubble trap, thus ensuring that it does not form a free jet as it enters the bubble trap. As infusate flows through the reduction chamber 200, the increasing width of the reduction chamber expands and slows the infusate stream. The slowed infusate stream rises in the hook shape of the reduction chamber 200 and flows over the bend 203, cascading from the upper portion of the reduction chamber 200 into the separation chamber 205. If used, the baffle 206 is positioned to confine the cascading infusate stream downwardly, through a channel along the wall 211, into the bottom of the separation chamber 205. The cascade of infusate into the separation chamber 205 enters the widest portion of the bubble trap 80, but encounters the sharp reduction in cross section in the transition to the laminar flow chamber 207, which sets up a recirculating flow pattern in the separation chamber 205. The narrow cross section in the laminar flow chamber 207 accelerates the infusate and forces it once more into a sheet that traverses the laminar flow chamber 207 across the hydrophobic membrane and past the sensor couplers 37A and 38A. The laminar stream of infusate enters the outlet chamber 215, where it is funneled into the short riser 219, which narrows and further accelerates the infusate flow and turns it toward the valve chamber 220 from which the infusate stream flows out of the warming cassette through the output port 71.

In FIG. 10, as the infusate flows through the trap flow path, the buoyancies of air boluses and large bubbles in the infusate pull them from the infusate stream as the stream flow slows through the reduction chamber 200. These large-diameter bubbles are collected in the reduction chamber 200. Thus, for example, bubbles 222 having diameters in the range of 1 to 3 mm, and larger, will separate from the stream of infusate and rise to be collected in the hooked upper portion of the reduction chamber 200. As the large bubbles rise and collect, they burst, which causes an air pocket 223 to form. As the infusate stream turns at the bend 203 and cascades into the separation chamber 205, bubbles remaining in the stream are circulated in the eddy of infusate in the separation chamber. This lengthens the dwell time of bubbles in the separation chamber 205, thereby increasing the likelihood that they will rise and burst, adding to the air pocket in the reduction chamber 200. Some small (1 mm diameter, for example) bubbles may be entrained into the eddy in the separation chamber 205 from foam at the border between an air pocket and the infusate; these bubbles tend to remain trapped in the eddy without passing to the laminar flow chamber 207. As the infusate stream passes through the laminar flow chamber 207 to the outlet chamber 215, very small bubbles remaining in the infusate are prevented by the hydrophilic screen 217 from leaving the outlet chamber 215. These small bubbles stick to the surface of the screen 217, but are not drawn through. Over time, multiple bubbles coalesce on the hydrophilic screen 217, forming larger bubbles with enough buoyancy to lift off the hydrophilic screen and rise to the top of the bubble trap 80. Air expelled with infusate from a bag may also enter the trap. As air accumulates in the top of the bubble trap 80, it is vented from the trap through the air vent 81 by the hydrophobic membrane 209 and the apertures 210. If the level of collected air in the bubble trap reaches the sensor couplers 37A and 38A the valve 82 is closed and infusate is stopped from flowing out of the warming cassette 60.

The hydrophobic membrane 209 provides preferential flow of gases over liquids and therefore draws air from the bubble trap 80 and releases it to the ambient atmosphere. Thus, the hydrophobic membrane 209 serves as a vent through which air is eliminated from the bubble trap 80. A representative construction of the hydrophobic membrane is shown in FIG. 13, wherein a 2-3 mil thick hydrophobic membrane constituted of a polymer material, preferably an expanded polytetrafluoroethylene (ePTFE) disc 225 having a nominal 0.45 micron pore size has a polyester nonwoven backing 227. We have obtained such a hydrophobic membrane from W.L. Gore & Associates. The membrane 209 has a disc-like shape and may be glued, bonded, or welded directly to the inner surface of the outer side 64o, with the polyester backing 227 in contact with the inner surface and the hydrophobic material facing the laminar chamber 207. The outer side 64o of the laminar flow chamber is outwardly contoured to provide a cylindrical ledge 229 on its inner surface to position and support the membrane 209, and a cylindrical vent chamber 230 to collect air passed through the membrane 209 from the bubble trap 80. Intermittent ridges 232 in the chamber 230 support the membrane 209 against the pressure of infusate flowing through the bubble trap 80, but do not impede the circulation of air in the vent chamber 230. Vent holes 210 (best seen in FIGS. 10 and 12A) permit air to pass from the bubble trap 80, through the outer side 64o, to the ambient atmosphere. With reference to FIGS. 12A and 13, an umbrella-shaped silicone check valve 234 is mounted on the outer surface of the outer side 64o by a central mounting hole 236. The outer rim 238 of the check valve 234 covers the openings 210. When the pressure of the air collected in the vent chamber 230 exceeds atmospheric pressure, the outer rim 238 yields and collected air passes through the openings 210 to the ambient atmosphere.

Figure 14A:
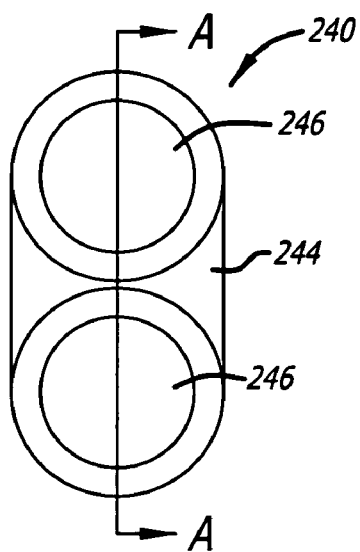
FIG. 14A is an enlarged plan view of a sensor coupler piece.
Figure 14B:
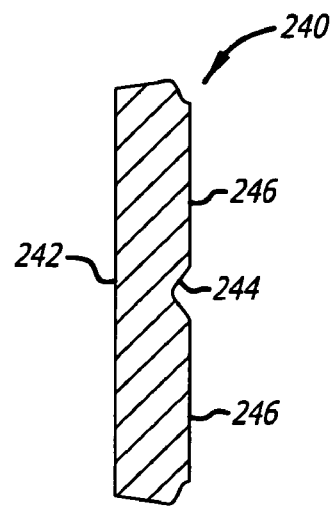
FIG. 14B is a longitudinal cross section of the sensor coupler piece.
Figure 15:
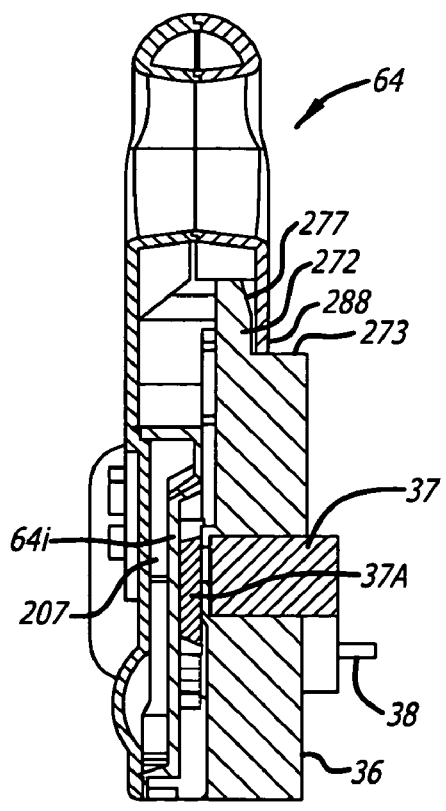
FIG. 15 is a partial side cross sectional view of an upper portion of the housing of FIG. 10 showing engagement between a sensor and a sensor coupler.

With reference to FIGS. 12B and 15, the sensors 37 and 38 sense the level of fluid (air and infusate, for example) and enable the detection of air in the bubble trap 80 for the purpose of controlling the flow of infusate. In some aspects, the sensors 37 and 38 may operate ultrasonically. In these instances, accurate sensing requires suppression of an echo reflected from an impedance mismatch such as solid/air transition at the rear face of the housing 64, which faces the sensors 37 and 38. The sensor couplers 37A and 38A mounted to the housing eliminate reflections of transmitted ultrasonic pulses from the rear face of the housing 64. A representative construction of the sensor couplers 37A and 38A is shown in FIGS. 14A and 14B. The sensor couplers 37A and 38A may be formed in a piece 240 of a relatively soft, but durable material that has a high transmissivity at ultrasonic wavelengths. The piece 240 has a flat, planar front surface 242 and a rear surface 244 on which domes 246 may be formed to increase coupling effectiveness. The domes 246 constitute the sensor couplers 37A and 38A. The front surface 242 of the piece 240 is adhered, bonded, or welded to the outside surface of the inner side 64i, adjacent the laminar flow chamber 207. Presume the warming cassette 60 is seated in the infusion unit 10 as shown in FIG. 2; then, as seen in FIG. 15, the faces of the sensors 37 and 38 are in intimate pressing contact with the sensor couplers 37A and 38A. The material of which the sensor couplers are constructed minimizes or eliminates reflection of transmitted ultrasonic pulses from the outside surface of the rear face of the housing 64 and passes echoes reflected from the inside surface of the front face of the housing 64. It is advantageous to have the sensor couplers 37A and 38A mounted to the housing 64 because the material of which the apertures are made can be less durable than if mounted to the mounting block 36 or the sensors 37 and 38. This is because the piece 240 has to undergo only a single use that occurs when the warming cassette is inserted in the infusion unit 10. The domes 246 formed on the piece 240 allow the material of which it is formed to displace more easily when in response to sensor contact, which makes the material appear even softer than if the sensors 37 and 38 displaced a flat planar surface. We use a sensor coupler piece 240 formed of injection-molded thermo-plastic elastomer (TPE) 5.175 mm thick, 30 durometer, shore A.

A representative construction of the hydrophilic screen 217 that filters small bubbles from the infusate path in the outlet chamber 215 of the bubble trap 80 is shown in FIG. 16. The hydrophilic screen 217 is constituted of a 263 micron nylon mesh 250 supported on a molded plastic support 252. We have obtained such a screen from GVS Filter Technology, Rome, Italy. The hydrophilic screen has an open end 254, and an opposite end (not visible in FIG. 16) which may be closed by an element of the molded plastic support 252. Referring again to FIG. 10, the open end 254 of the resulting thimble-like structure is glued, bonded, welded, or fitted to the outlet structure of the outlet chamber 215, in fluid communication with the inlet to the riser 219.

Figure 17:
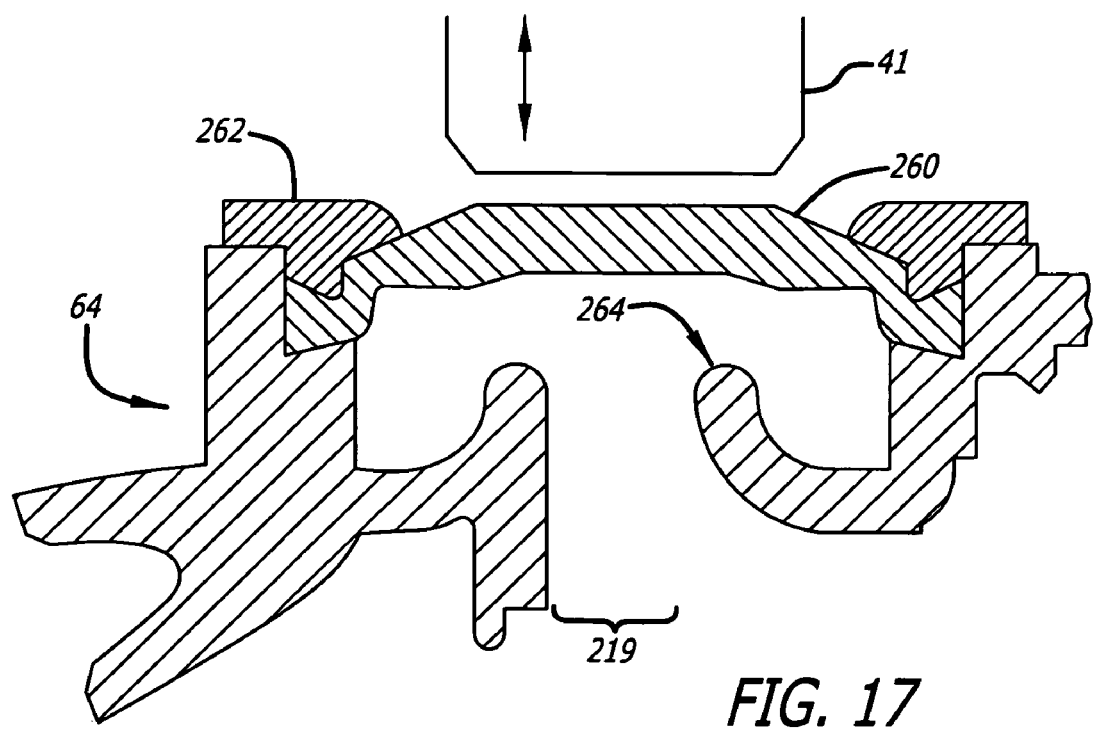
FIG. 17 is an enlarged side sectional view of a valve in fluid engagement with the bubble trap in the housing of FIG. 10.

With reference to FIGS. 12B, and 17, the valve 82 includes the circular valve chamber 220, a valve membrane 260, and a seating ring 262. The valve membrane 260 is disposed over a second side of the circular valve chamber 220 and held thereto by the seating ring 262. When the piston 41 is retracted, the valve 82 is open; to close the valve 82, the actuator 40 is activated, which throws the piston 41 against the valve membrane 260, forcing the membrane against the open end 264 of the riser 219. This prevents infusate from flowing into the circular valve chamber 220 and out of the output port 71. Preferably, the valve membrane 260 may be formed of silicone or any other durable, flexible material that is compatible with blood. We have obtained such a silicone valve membrane from Liquid Molding Systems, Midland, Mich. Alternately, the valve 82 could be constituted of a rigid, electromechanically-actuated valve, such as a quarter-turn stopcock.

Heat Exchanger Installation and Retention

Use and operation of the high flow rate infusion unit are simplified by an interlocking mechanical interface between the infusion unit and heat exchanger that enables an operator to quickly and easily install the heat exchanger, bubble trap, and shut off valve in a single act. By sliding the heat exchanger into position between the heating plates, the operator positions the laminar flow path for heat exchange, locates the bubble trap for monitoring by the sensors 37 and 38, and orients the shut off valve for operation.

Considering the exemplary embodiment of the heat exchanger, when the warming cassette is installed in the high flow rate infusion unit, various elements of the warming cassette 60 and the infusion unit 10 cooperate to seat the warming cassette and to enable the infusion unit to control the flow of infusate. In this regard, with reference to FIGS. 18 and 19, the housing 64 engages the mounting block 36 and rests on the bezel 32. The warming cassette is thus retained in place against the mounting block 36, and supported by the mounting block 36 and the bezel 32, when installed. In this position, the fluid container 62 is aligned in operable engagement with the heating plates, the sensor couplers 37A and 38A are aligned in operable engagement with the sensors 37 and 38, and the valve membrane 260 is aligned in operable engagement with the piston 41.

Figure 18:
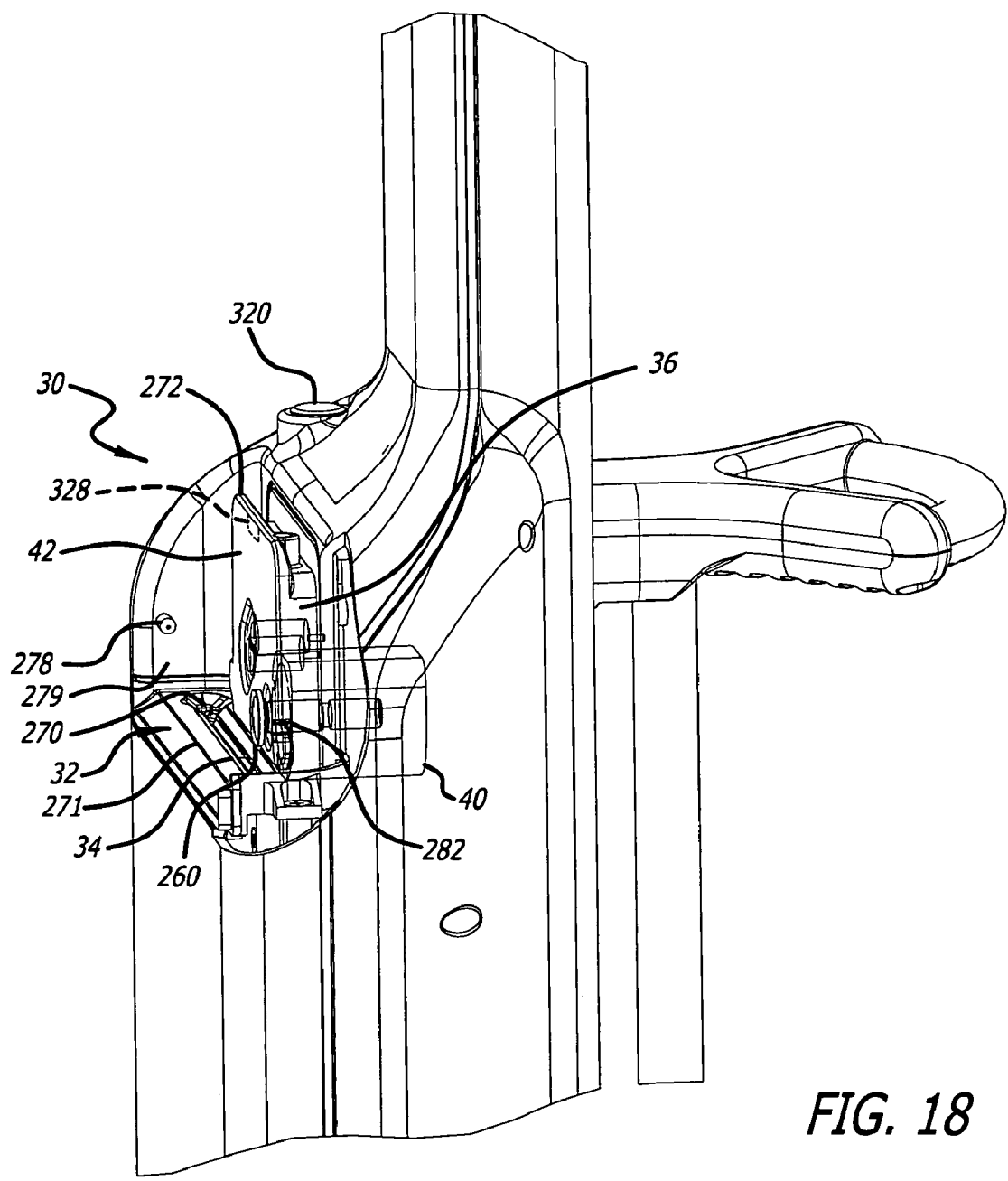
FIG. 18 is an enlarged perspective view of the side of the high flow rate infusion unit partially cut away to illustrate construction details.
Figure 19:
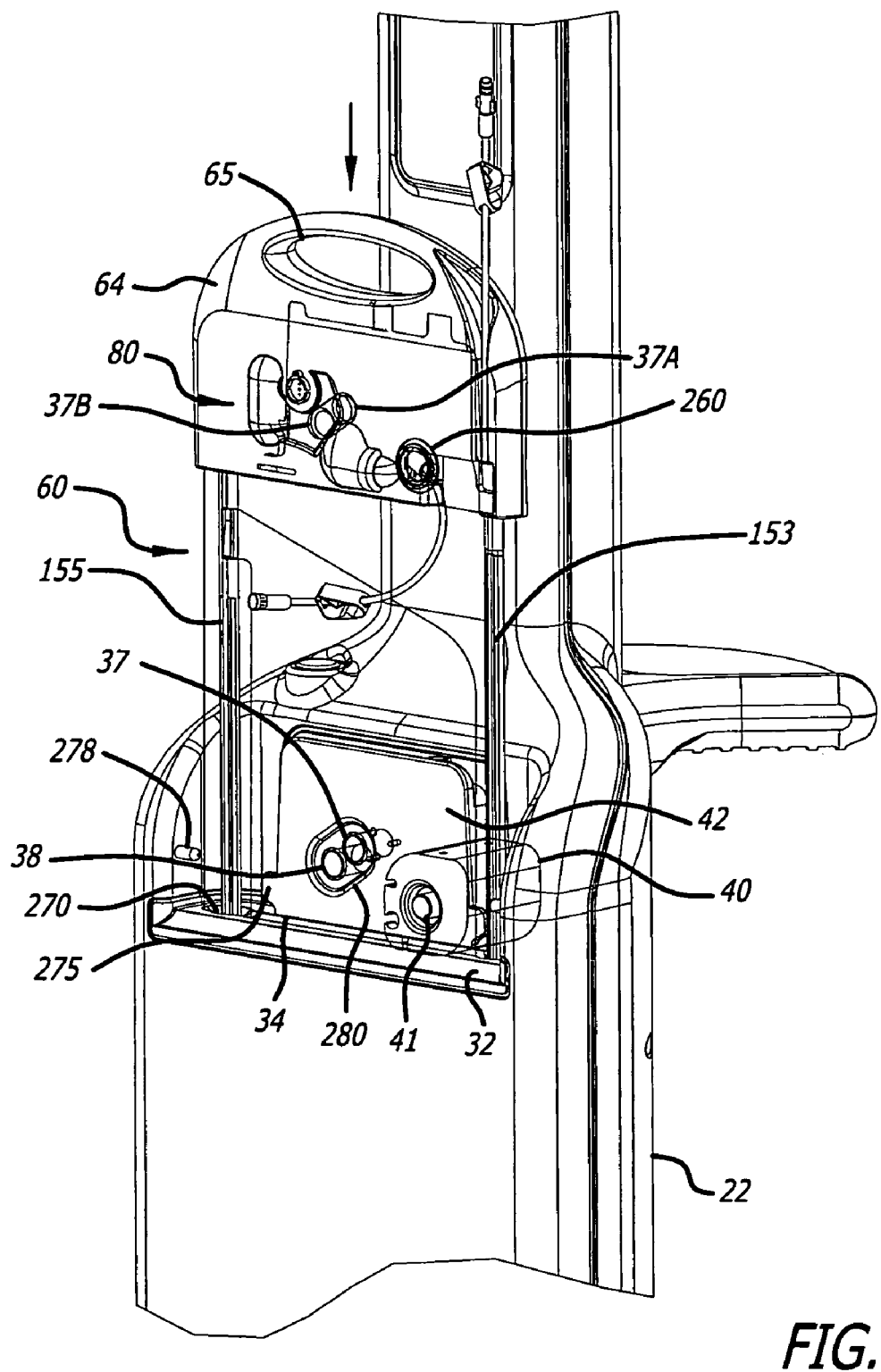
FIG. 19 is an enlarged perspective view of the front of the high flow rate infusion unit with the warming cassette partially inserted into the high flow rate infusion unit.

With reference to FIG. 19, a warming cassette 60 is partially installed in the infusion unit 10, with its distal end 61 having been received in the slot 34 and its rails in the circular enlargements 270. As downward pressure is exerted on the warming cassette 60, the housing 64 moves toward the bezel 32. Construction details of the bezel 32 are shown in FIG. 18. The bezel 32 is fixedly mounted on flat planar area of the recessed surface portion 30, oriented transversely to the pedestal 22. The mounting block 36 is fixedly mounted in the recessed surface portion 30, disposed substantially perpendicularly to and abutting an inside edge of the bezel 32. The slot 34 in the bezel 32 is oriented transversely to the pedestal 22 and in parallel with the major surface 42 of the mounting block 36. The slot 34 is aligned with the narrow laminar space between the heating plates and includes a diamond shaped, oval, or round enlargement at each end to accommodate the rails of a warming cassette. Each circular enlargement is aligned with the elongate parallel channels formed by the elongate parallel grooves of the heating plates (See FIGS. 8 and 9). One such circular enlargement 270 is seen in FIG. 18. The bezel 32 is therefore constructed to receive a warming cassette, distal end first, in the slot 34, with the rails of the warming cassette received in the circular enlargements 270 so as to guide the fluid container of the warming cassette into the narrow laminar space between the heating plates for seating therebetween. As is evident from FIG. 18, the bezel 32 forms a raised frame to support the housing 64, and includes a forward edge 271 that slopes downwardly and away from the slot 34.

As seen in FIGS. 12B and 18, a thin flange 272 projects from an edge 273 of the mounting block 36; the front surface of the flange 272 forms a portion of the major surface 42. A sensor 274 is mounted adjacent the rear side of the flange 272, on the edge 273. Preferably, the sensor 274 is an inductive proximity sensor. Two tabs 275 protrude outwardly in opposite directions from the bottoms of the lateral edges of the mounting block 36. One tab 275 is seen in FIG. 12B; its opposite is seen in FIG. 19. The rear side of the flange 272 has a recess with a projecting notch 276 near the edge 273. FIG. 15 shows that the flange 272 is wedge-shaped in its upper extent 277. A pair of retaining pins is fixedly mounted in opposing relationship to the opposing sides of the recessed surface portion 30 of the infusion unit pedestal 22. One of the retaining pins 278 can be seen on one of the opposing sides 279 in FIG. 18. As seen in FIGS. 12B, 18 and 19, a sloped elongate trench 280 with rounded ends in the major surface 42 surrounds the locations of the sensors 37 and 38, which protrude beyond the plane of the major surface 42, toward the housing 64. When a warming cassette is installed, the rear face of the housing 64 is slightly separated from the major surface 42. When the housing engages and latches to the mounting block 36, the sensor couplers 37A and 38A on the rear face of the cassette housing align with and contact the faces of the sensors 37 and 38, and retain the sensors in engagement while the warming cassette is installed in the infusion unit. FIGS. 12B and 18 also show the actuator 40 mounted to the back of the mounting block 36 aligned with a through the hole 282 through which the piston 41 is moved back and forth.

A cutout 286 with an upper edge 288 in the rear face of the housing 64 is visible in FIG. 12B. The cutout 286 is shaped to accommodate the shape and dimensions of the mounting block major surface 42. As best seen in FIGS. 12B and 15, inner side 64i of the housing 60 is inset from the cutout 286. FIG. 12B shows a slot 290 in the upper edge 288 and a metallic strip 291 mounted in the housing adjacent the slot 290. FIG. 12B also shows an upper flexible tab 292 formed in the upper edge 288. Two spaced-apart flexible tabs inset from the upper edge 288 are formed in the lower portion of the housing 64. One of the tabs 293 is seen in FIG. 12B.

With reference to FIG. 19, the warming cassette 60 is installed in the infusion unit 10 by orienting the rear face of the housing 64 to face the infusion unit 10 and then sliding the distal end 61 into the bezel slot 34, with the rails 153 and 155 received in the circular enlargements 270. With reference to FIG. 15, as the warming cassette 60 slides home, the upper edge 288 of the housing cutout 286 engages and slides along the wedge-shaped upper extent 277 on the back of the mounting block's flange 272, and (as shown in FIG. 20) the front face of the housing slides along the inner sides of the retaining pins 278. The inner side 64i is inset from the cutout 286 and spaced by a small gap from the major surface 42 of the mounting block 36. As the upper edge 288 of the housing cutout approaches the ledge 273, the slot 290 in the upper edge 288 aligns with and accommodates the sensor 274 on the mounting block 36, and metallic strip 291 is located near the sensor 274. With reference to FIG. 12B, the flexible tab 292 in the upper edge 288 aligns with and latches to the projecting notch 276 on the back of the flange 272, and further movement of the warming cassette 60 is stopped when the cutout upper edge 288 meets the ledge 273 of the mounting block 36, and the lower edge of the housing 64 meets the upper surface of the bezel 32. The warming cassette is now installed in the infusion unit 10 (as shown in FIG. 20), with the fluid container 62 seated between and in contact with the heating plates (see FIGS. 7-9), and with the sensor couplers 37A and 38A aligned and in contact with the sensors 37 and 38, and the valve membrane 260 aligned with the piston 41 (see FIGS. 12B, 20, and 21). The warming cassette is guided by the pins 278 into retention in the installed position by engagement between the upper edge 288 and the rear of the flange 272, engagement between the tabs 293 and the tabs 275, and locking of the flexible latch 292 to the notch 276. The warming cassette is released by disengaging the flexible latch from the notch while pulling upwardly on the housing 64.

Figure 21:
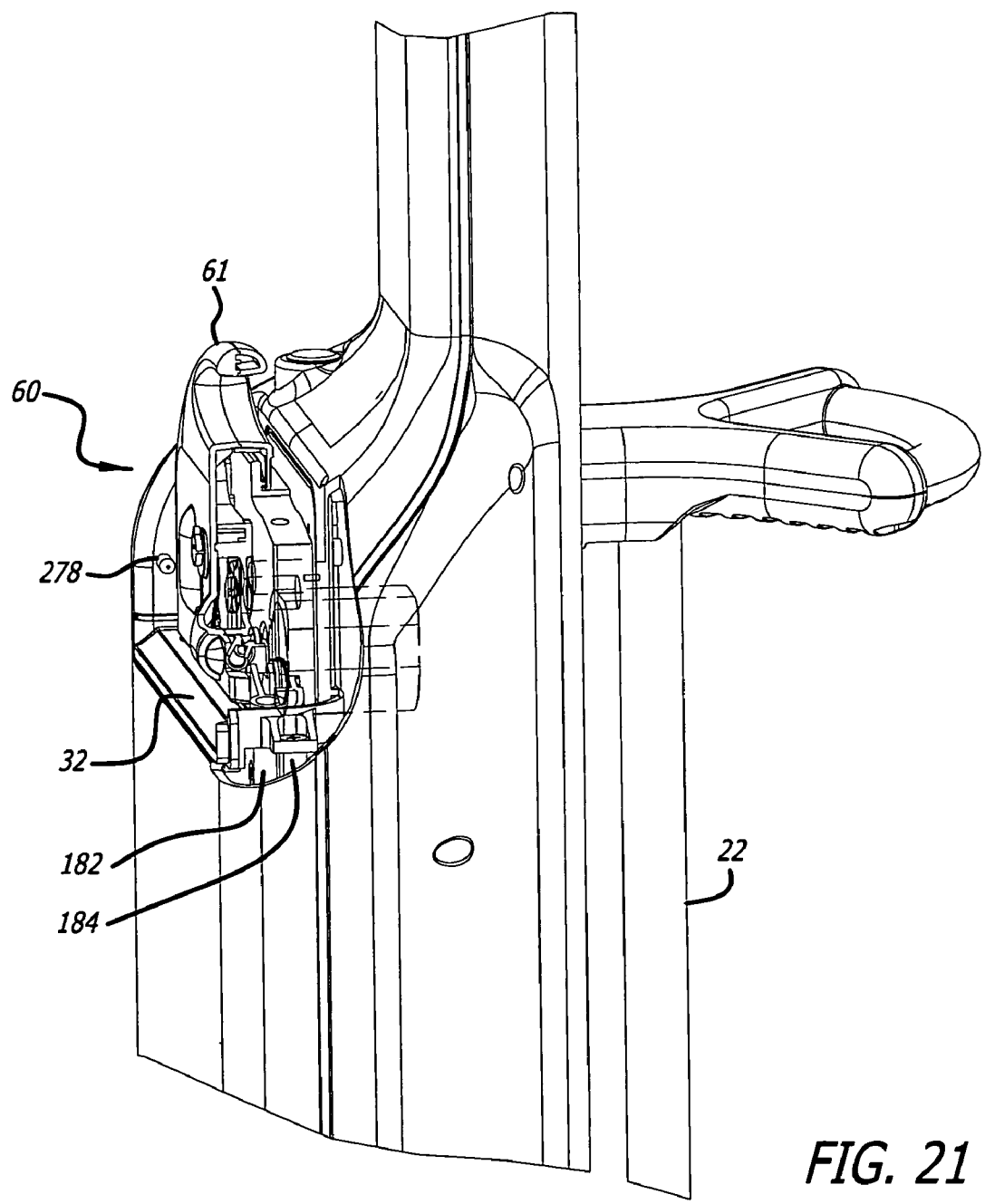
FIG. 21 is an enlarged perspective view of the side of the high flow rate infusion unit with the warming cassette seated therein and with the warming cassette and infusion unit partially cut away to illustrate construction details.

Audible and tactile feedback indicating that the warming cassette is completely seated is provided to an operator by the latching action of the tab 292 and the stopping of the housing 64 by the ledge 273. As best seen in FIGS. 20 and 21, the lower front and side edges of the housing 64 surround and shroud the bezel slot 34 so that the housing 64 shrouds the slot 34, enclosing and covering it to prevent fluid that might reach the bezel 32 from leaks in infusate bags, IV lines, or the housing 64 from flowing thereinto.

Infusion Unit Subsystems

The high flow rate infusion unit includes an electronic control subsystem with input, logic, and output elements that receive command and sensor inputs, process the inputs to set or change the control configuration of the unit during operation, and produce outputs that implement the current control configuration. The electronic control subsystem is assembled from conventional electrical, electronic, and electro-mechanical components mounted conventionally by means of printed circuit boards and structural elements in the neck and pedestal of the infusion unit. The electronic control subsystem is illustrated in FIG. 22.

Figure 22:
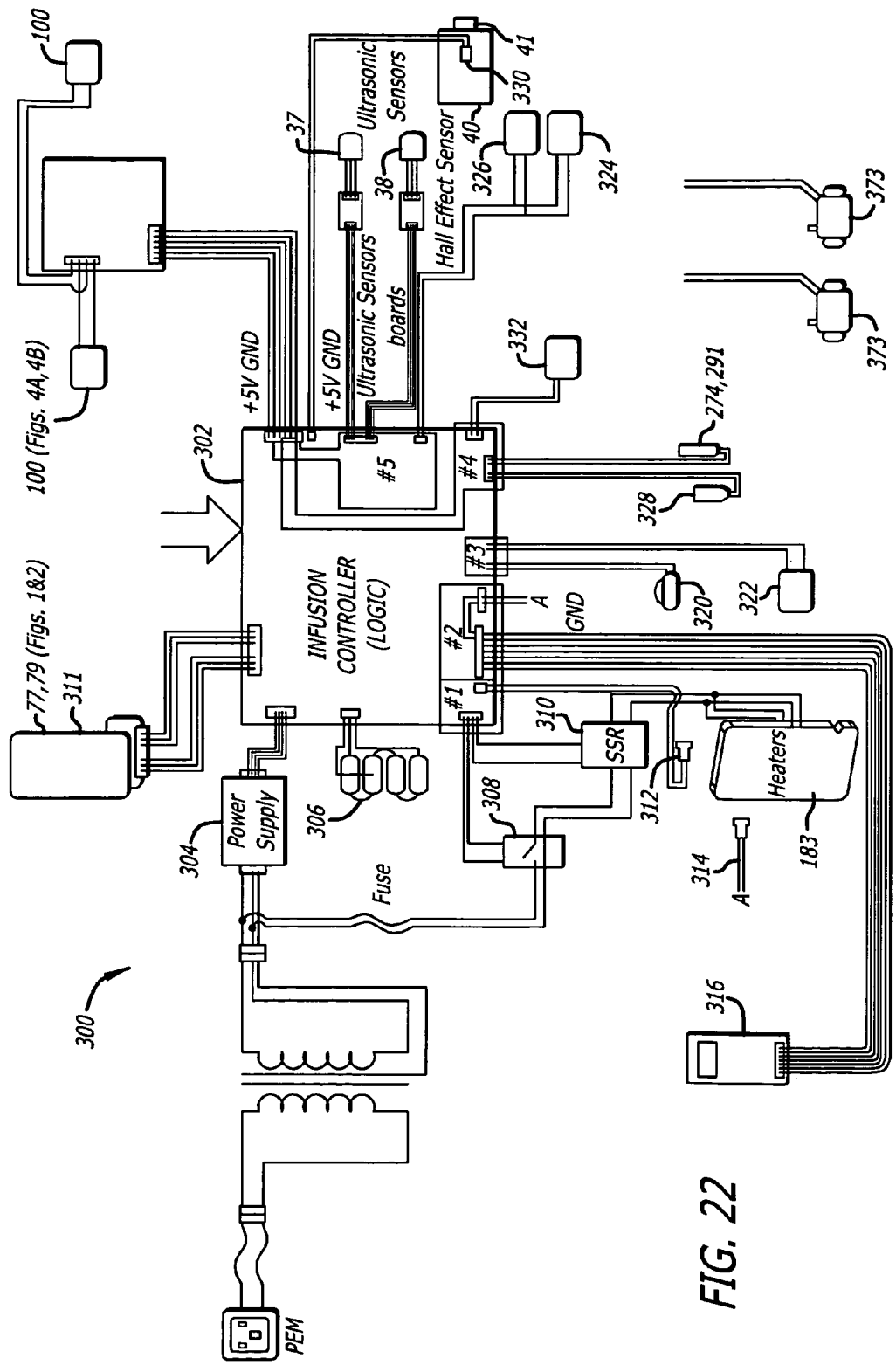
FIG. 22 is a block diagram representing an electronic control subsystem for the infusion unit of FIGS. 1 and 2.

In FIG. 22, the electronic control system ("control subsystem") 300 includes a controller 302 having at least five logic blocks labeled #1-#5. Preferably, the controller 302 is assembled using discrete components conventionally mounted to one or more circuit boards. However, the controller 302 may also be assembled from programmable and/or programmed elements including general or special purpose processors, programmable logic arrays, and other equivalent components. Inputs to the controller 302 are received from a power supply 304 and a battery pack 306. The power supply operates conventionally, converting AC mains power to various DC power outputs. The battery pack provides standby DC power to operate the controller 302 and control subsystem components in the event that operation of the power supply 304 is interrupted. AC mains power is provided to operate the heaters 183 through a power relay 308 and a solid state relay (SSR) 310. Both relays must be closed in order for AC power to reach the heaters 183. Opening either relay will interrupt the supply of AC power to the heaters 183, thereby causing the interruption of heat supplied to infusate flowing through a warming cassette seated between the heating plates 182 and 184. An operator interface 311 (including the control panels 77, 79 in FIGS. 1 and 2) provides means by which an operator can input commands and means to output information to the operator.

With further reference to FIG. 22, logic block #1 of the controller 302 executes a fail safe control function based upon comparison of a temperature measured by a thermistor 312 with a threshold temperature to turn off power to the SSR 310. The thermistor 312 measures a temperature of the heating plate 182. If the measured temperature should exceed the threshold temperature, the logic block #1 generates signals to open the relay 308, thereby blocking the provision of AC power to the SSR 310 and thus to the heaters 183.

With further reference to FIG. 22, logic block #2 of the controller 302 mediates a temperature control function that is based upon a set point temperature and an input from a resistance temperature detector (RTD) 314 that measures a temperature of the heating plate 184. In this regard, a temperature-influenced resistance measured by the RTD 314 is provided to a controller 316 and converted to a temperature value by the controller. The controller 316 executes a temperature control function to maintain the measured temperature at a set point value by turning the SSR 310 on and off as needed to keep the measured temperature at the set point temperature. Control signals produced by the controller 316 are passed to the SSR 310.

With reference to FIG. 7, the thermistor 312 is mounted in the hole 194 in the heating plate 182, and the RTD 314 is mounted in the hole 193 in the heating plate 184, opposite the thermistor. As is evident from the figure, the thermistor 312 and RTD 314 are located in the transverse channels 192 formed in the surfaces of the heating plates that cause the formation of a manifold in the fluid container 62 that channels infusate from the laminar flow path 67 into the slot 166 in the rail 155. Thus, with accounting for heat transfer through the fluid container, the thermistor 312 and the RTD 314 effectively measure the temperature of the heated infusate as it enters the bubble trap. Thus, the controller 316 operates to maintain the temperature of warmed infusate flowing into the bubble trap 80 at the set point. In logic block #1, if the temperature of warmed infusate flowing into the bubble trap 80 as measured by the thermistor 312 exceeds the threshold temperature (which preferably is the sum of the set point temperature and a predetermined safety margin), the power relay is signaled to shut off AC power to the SSR 310. For example, we have used a set point temperature of 42° C., and a threshold temperature of 46° C.

In FIG. 22, logic block #3 responds to activation of a release button 320 by an operator signaling that a warming cassette is to be extracted from the infusion unit. As seen in FIG. 18, the release button 320 is located on the top of the pedestal 22, adjacent the recessed surface portion 30. Preferably, the release button is a manually operated, push button switch, although it may also be embodied as a pressure activated electronic switch or a touch screen icon. Through logic block #3, activation of the release button 320 assists in releasing a warming cassette from engagement with the infusion unit by dislodging the warming cassette from the warming plates 182 and 184 and withdrawing the piston 41 from contact with the valve 82. In this regard, the warming cassette may be dislodged by activating an electronically controlled pneumatic valve 322 to release one or more jets of pressurized air which pass through the holes 195 in the heating plates 182 and 184 seen in FIG. 7. The piston position is determined by the conditions of electronically controlled pneumatic valves 324 and 326.

Logic block #4 of the controller 302 seen in FIG. 22 monitors the sensor 274 seen in FIG. 12B. When the sensor 274 senses close proximity of the metallic strip 291 (as would occur when the housing was seated on the mounting block 36), it produces a signal interpreted as confirming the presence of a warming cassette properly aligned with and seated in the infusion unit 10. Alternately, when the sensor 274 senses close proximity of the metallic strip 291, the signal produced may be interpreted as confirming the presence of the bubble trap 80 and proper alignment of the valve 82 with the actuator 40 in the infusion unit. With reference to FIGS. 18 and 22, in some aspects, a photosensor 328 may be provided on the mounting block 36 to provide an initial indication of the presence of the housing 64 near the mounting block, following which the sensor 274 will respond to close proximity of the metallic strip 291 to provide an indication that the housing has been properly seated on the mounting block in the manner previously explained. In this case, concurrent outputs from the sensors 274 and 328 is interpreted as confirming correct installation of a warming cassette with its fluid container seated between the heating plates. Logic block #4 also provides control signals for activating an electronically controlled pneumatic valve 332 that controls pressure in an air reservoir (not seen).

Logic block #5 of the controller 302 seen in FIG. 22 receives and processes signals output by the ultrasonic sensors 37 and 38 that indicate the presence of a fluid (air or infusate) in the bubble trap, and signals output by a Hall effect sensor 330 in the actuator 40 that indicates the position of the piston 41. As an additional safety measure, logic block #5 provides control signals for activating the ON/OFF function of the pressure infusers.

The high flow rate infusion unit includes a pneumatic subsystem with elements that receive signals from the electronic control subsystem 300 indicating the control configuration of the unit during operation, and respond to the inputs by setting or changing the operational pneumatic configuration. The pneumatic subsystem also includes sensors that provide signals to the electronic control subsystem 300. The pneumatic subsystem is assembled from conventional pneumatic components mounted conventionally by means of structural elements in the neck and pedestal of the infusion unit.

Figure 23:
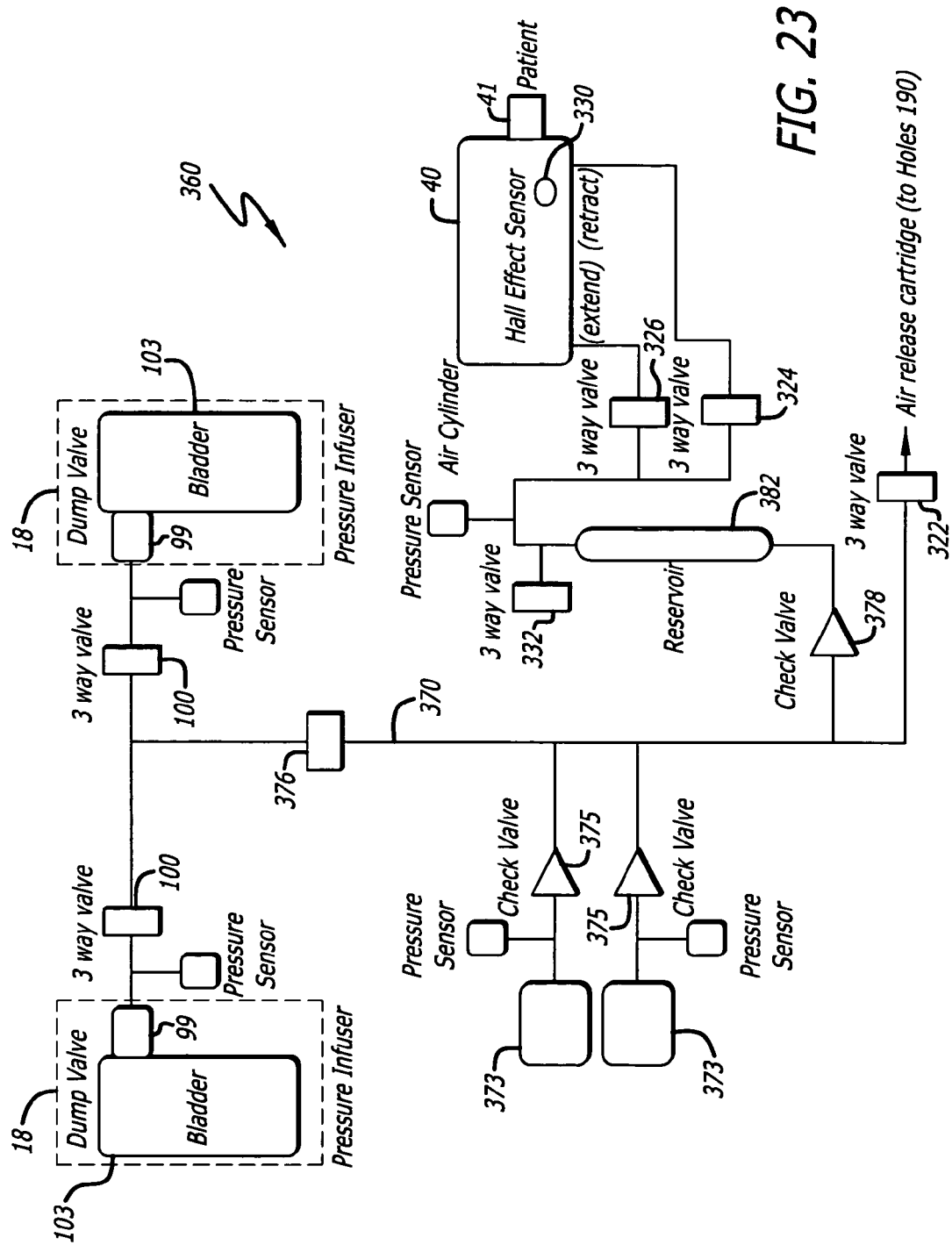
FIG. 23 is a schematic diagram representing a pneumatic subsystem for the infusion unit of FIGS. 1 and 2.

With reference to FIG. 23, the pneumatic subsystem 360 includes a main distribution channel 370. Pressurized air is provided to the distribution channel 370 from dual pumps 373, operating in parallel, via check valves 375. The dual pump configuration is preferred for enhanced performance under normal operating conditions and also for safety reasons. Both pumps operate while the infusion unit is warming infusate; if either pump fails during infusion, the remaining pump has the capacity to carry on the operations necessary to keep the pneumatic subsystem operating.

With further reference to FIG. 23, pressurized air in the distribution channel 370 flows to the electronically controlled three way valves in the pressure infusers 18 through a pressure regulator 376; pressurized air in the distribution channel 370 flows through a check valve 378 to the electronically controlled valves 324 and 326 which are preferably three way valves; and pressurized air in the distribution channel 370 flows to the electronically controlled valve 322 which is preferably a three way valve. The valve configuration in the pressure infusers 18 is not limiting; many other configurations may be used.

With reference to FIGS. 4A, 4B, and 23, logic block #5 (FIG. 22) allows the pressure infusers 18 to turn ON/OFF, or not. In this regard, each three way valve 100 in the pressure infusers 18 is controlled electronically via logic block #5 in the controller 302 to connect either the ambient atmosphere or the distribution channel 370 to its associated dump valve 99. When a pressure infuser 18 is operated, its three way valve 100 is operated to connect the distribution channel 370 to the associated dump valve 99, which causes pressurized air to inflate the associated bladder 103, thereby forcing infusate from a bag B in the pressure infuser. When the bag B is empty, when infusion is completed, or in other appropriate circumstances, the valve 100 is operated to connect the ambient atmosphere to the associated dump valve 99, which causes pressurized air in the associated inflated bladder 103 to flow out of the dump valve to the atmosphere, thereby deflating the bladder 103.

With reference to FIGS. 22, and 23, pressurized air flows through the check valve 378 into the reservoir 382. The three way valve 332 is controlled electronically via logic block #4 to connect the output of the reservoir 382 to either the ambient atmosphere or the inputs of the valves 324 and 326. Preferably, the actuator 40 is a double acting pneumatic piston actuator conventionally operated by pressurized air provided by the valves 324 and 326. The valves 324 and 326 are operated 180° out of phase by logic block #5 to position the piston 41 at an extended position against the valve membrane 260, which closes the valve 82, or a retracted position away from the valve membrane 260, which opens the valve 82. When the pumps 373 are turned off and the release button 320 is operated, the states of the three way valves 324 and 326 are configured by logic block #3 for withdrawal of the piston 41 to the retracted position and pressurized air from the pumps 373 and in the reservoir 382 is provided to the three way valves to move the piston to the retracted position. If the piston 41 is in the retracted position and the warming cassette 60 is extracted when the pumps 373 are turned off and the release button 320 is operated, the state of the three way valve 332 is set to vent the contents of the reservoir 382 to the ambient atmosphere.

With reference to FIGS. 7, 22, and 23, the three way valve 322 is controlled electronically via logic block #3 in the controller 302 to connect either the ambient atmosphere or the distribution channel 370 to the holes 195 in the heating plates 182 and 184. When the release button 320 is operated, the three way valve 322 is configured to connect the distribution channel 370 to the holes 195, thereby jetting pressurized air therethrough which breaks away surface tension and pushes fluid out of the fluid container 62. Otherwise, the valve 322 is configured to connect the ambient atmosphere to, or to close, the holes 195.

Method of Operation

Figure 24:
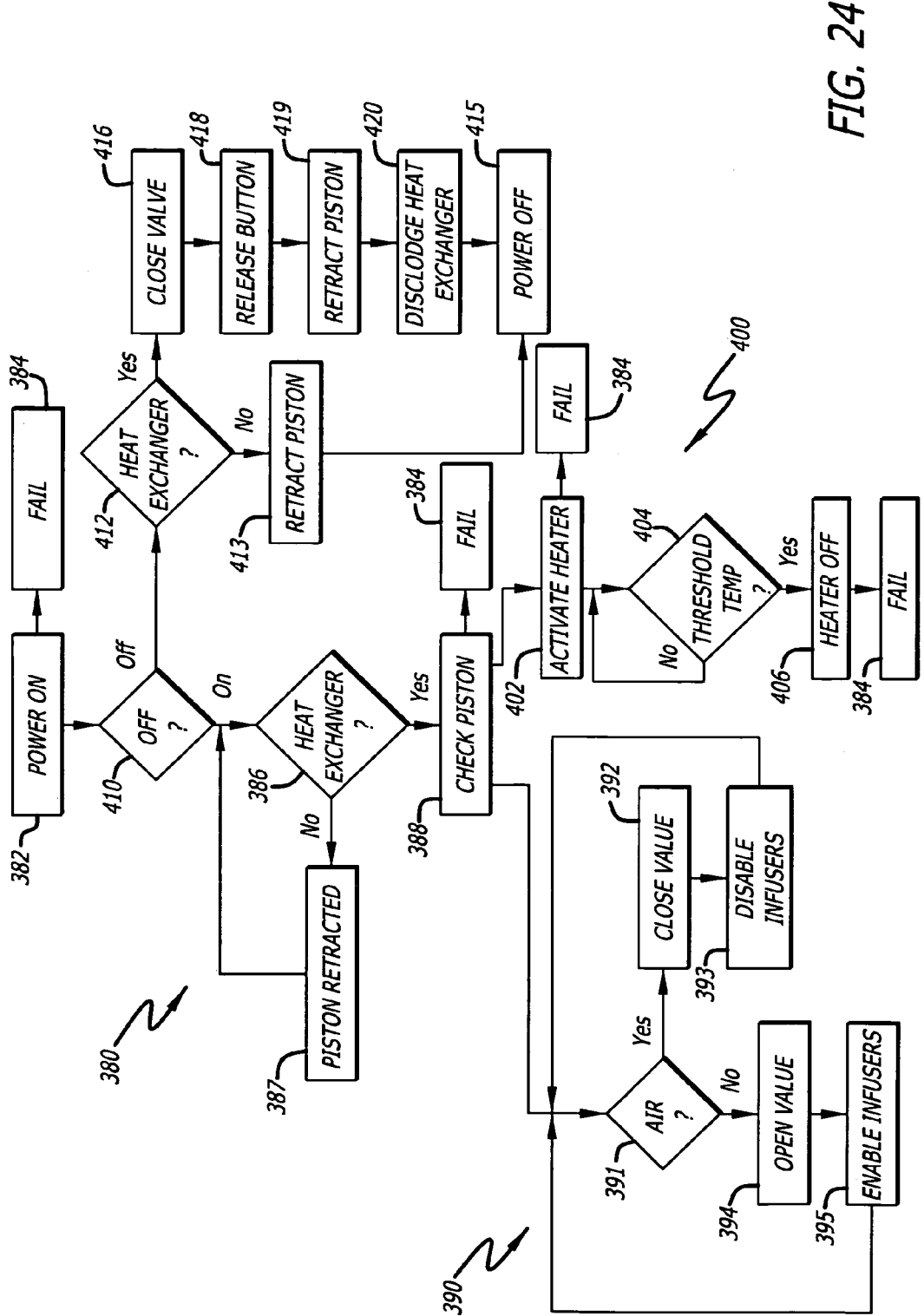
FIG. 24 is a flow diagram illustrating operation of the high flow rate infusion unit in conjunction with the heat exchanger.

The high flow rate infusion unit 10 with the heat exchanger 12 illustrated in FIGS. 1 and 2 may be operated according to a method shown in the flow diagram of FIG. 24. With reference to FIGS. 1, 2, and 24, the method of operation 380 preferably initiates from a power on state 382 in which power is initially supplied to the infusion unit 10, with or without a heat exchanger 12 (for example, the warming cassette 60) installed. During initiation of operation, electronics, pneumatics, and logic are tested. If anomalies are found, the method exits to a failure mode 384, where one or more status indicators are provided on the infusion unit's operator interface. With power successfully turned on, the method checks for installation of the heat exchanger at 386. If no heat exchanger is installed, the method of operation ensures that the piston 41 is retracted at 387 and operation suspends at 385 until a heat exchanger, installed with its planar flow path seated in the heating unit, is detected. With a heat exchanger installed, correct operation of the piston 41 is validated at 388 by, for example, three successive oscillations between the retracted and extended positions. Failure at 388 causes the method to exit to a failure mode 384. Otherwise, the method 380 branches to concurrently executing air management and heater control loops.

In this explanation, air management is based on a test for the presence of a fluid such as infusate or air in the bubble trap. In FIGS. 2 and 24, during the air management loop 390, the bubble trap 80 is checked (by the sensors 37 and 38, for example) for the presence of air at 391 In this regard, it is preferred that, when a heat exchanger 12 is installed, it will be connected to an infusate bag for priming. Preferably, but not necessarily, the bag will be located in a pressure infuser 18. The heat exchanger 12 will be primed by gravitational flow of infusate to and through the laminar flow path. Air will be expelled through the bubble trap vent, permitting the priming infusate to flow into and fill the bubble trap 80. While the heat exchanger 12 is being primed, air will be detected and the air management loop 390 will transition through 392 and 393, keeping the valve 82 closed and disabling the pneumatic subsystem from inflating the infusion bladders 103 shown in FIGS. 4A and 4B (by configuration of the three way valves 100, for example). When the bubble trap 80 has been filled to a level at which the sensors no longer detect air, the air management loop 390 will transition through 394 and 395, opening the valve 82 and enabling operator action for starting the pneumatic subsystem to inflate the infusion bladders 103. That is to say, the controller 302 will open the valve 82, but will not initiate inflation. Instead an operator is prompted by an alarm or other indication to use the operator interface 311 to activate a pressure infuser. In this regard, the operator will input a command via the interface 311 causing a pressure infuser to activate. Thereafter, during infusion, the air management loop 390 operates in response to the presence or absence of air in the bubble trap by taking the appropriate transition from 391. In the transition 391, 394, 395, 391, no action is required at 394 if the valve 82 is open or at 395 if the pressure infusers are enabled. When a bag of infusate has been emptied or is near empty in one pressure infuser, the operator reconfigures the Y tube set 73 to stream infusate from a full bag in the other pressure infuser. Using the interface 311, the operator will stop operation of the pressure infuser with the empty bag and start operation of the other pressure infuser. In response to the stop/start indications from the operator, the controller 302 (FIG. 22) operates the three way valves 100 to deflate the bladder 103 in the stopped pressure infuser and to inflate the bladder in the pressure infuser with the full bag. To continue infusion, the operator replaces the empty bag in the stopped pressure infuser with a full one.

An important safety feature of the air control loop is realized in closing the valve 82 and stopping infusion when air is detected. If the valve 82 should leak under the pressure of the infusate when closed, air might pass with leaking infusate through the closed but leaking valve. Deflating the active bladder relieves the pressure on the closed valve, thereby reducing, if not eliminating the risk of air leaking through the closed valve.

With reference to FIGS. 22 and 24, the heater control loop 400 is initiated at 402 by initiating the controller 316, turning on the heaters 183, and bringing the heating unit to the set point temperature. If turn on fails to execute properly, the method exits to a failure mode 384. After successful turn on, control of heating plate temperature for set point operation is implemented by operation of the set point controller 316. While the heating plates operate, the controller 302 continuously checks the fail safe control function at 404. If the threshold temperature is exceeded, the heating plates are turned off at 406 and a failure mode 384 is entered.

With reference to FIG. 24, the method of operation continuously checks the status of all infusion unit processes during all operations. Failure modes are dealt with as appropriate to the particular circumstances of failure. In most instances, the controller 302 responds to a failure mode by deflating the balloons 103 in the pressure infusers 18, closing the valve 82, and providing audible and visual indicators via the interface 311. Operator action, such as selection of an "OFF" button or condition to turn the infusion unit off when an infusion is terminated and system operation is to be ceased will trigger power off status. In some instances an operator may also select an "OFF" button or condition when a heat exchanger is not installed in the infusion unit 10. For these cases, and in other appropriate circumstances, once power on has been successfully completed, the method of operation 380 continuously monitors a power off test at 410. If a power off condition is active, the method terminates all currently active processes, including the air management and heater control loops, and transitions to 412, testing whether a heat exchanger is installed in the infusion unit 10. If a heat exchanger is not installed, the method ensures that the piston 41 is retracted at 413, and then completes action by transitioning to a power off state at 415 wherein all processes are terminated and power is turned off. If a heat exchanger is detected at 412, the method 380 ensures that the valve 82 is closed and the pressure infusers are disabled (if not already turned off by the operator) at 416 so that infusate flow to the patient line and to the heat exchanger is stopped. When the release button is activated at 418, the method retracts the piston 41 at 419 and dislodges the heat exchanger at 420. In this regard, for the warming cassette embodiment, dislodging at 420 includes operating the pneumatic subsystem to jet compressed air through the holes 195 to disengage the fluid container 62 from the heating plates 182 and 184. The method then transitions to the power off state at 415.

Air Sensing and Management

Preferably, air is sensed in the bubble trap by one or more sensors mounted in the infusion unit 10; preferably, at least two such sensors are used in order to provide redundancy, operational hysteresis, and a rich logical control mechanism for air management. We have used ultrasonic sensors that operate like sonar devices by transmitting and receiving pulses of ultrasonic energy. In particular, each of the sensors 37 and 38 may comprise a ceramic pulse echo sensor embedded potted, or screw mounted in a respective anodized hole through the mounting block 36. In operation, each sensor sends out an ultrasonic pulse through a medium, and detects an echo of the pulse reflected back to the sensor off of an impedance mismatch, such as occurs at a solid/air interface. One source of such sensors is the Zevex Applied Technology Division, Salt Lake City, Ut.

Figure 25:
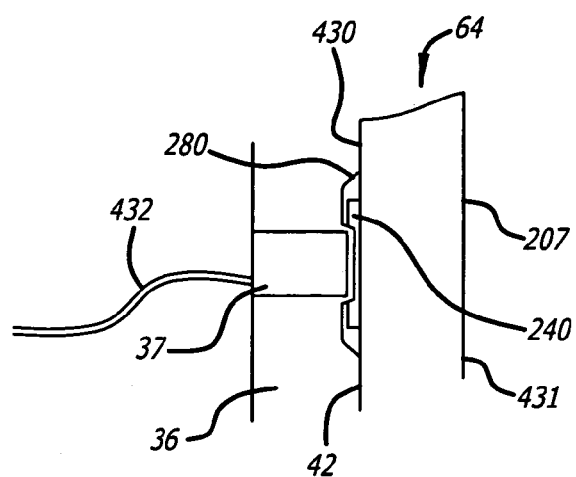
FIG. 25 is a schematic diagram of a sensor in operational engagement with the bubble seen in FIG. 10.

As seen in FIGS. 12B and 25, the sensors protrude through the major surface 42 of the mounting block 36 and face the rear face 389 of the housing 60, in contact with the sensor couplers 37A and 38A formed on the material piece 240. Presume that the sensor 37 emits a pulse of ultrasonic energy. The sensor pulse enters the coupler 37A, and travels through the material piece 240 and the rear face 430. Because of the insignificant difference in impedance between the sensor coupler and housing materials, no echo is produced by the outside surface of the rear face 430. If the level of infusate is above the position of the sensor coupler 37A, the pulse travels through infusate in the housing to the front face 431, and an echo is produced by the solid/air discontinuity at the outside surface of the front face. The front face echo travels back, through the infusate, the rear face, and the material piece 240 and is detected by the sensor 37. If, however, the level of infusate is below the position of the sensor coupler 37A, the transmitted pulse meets an impedance discontinuity at the solid/air interface between the rear face of the housing and air in the bubble trap, and an echo is produced by the rear face 431. The rear face echo travels through the material piece 240 and is detected by the sensor 37. Manifestly, the elapsed time to detect the front face echo is longer than that for the rear face echo. The sensor 37 provides a signal indicative of the elapsed time on a conductor 432 to the controller 302. The signal is interpreted as indicating the absence or presence of air (or, conversely, the presence or absence of infusate) in the bubble trap 80. The consequence of the difference in elapsed time is that absence of a rear face echo is interpreted as the presence of infusate (or, conversely, as the absence of air), while detection of a rear face echo is interpreted as the presence of air (or as the absence of infusate). Logic provided in the sensor utilizes a pulse window beginning with the transmission of a pulse having a width wide enough for a pulse to travel to and from the front face. An echo received within the pulse window is interpreted as indicating the presence of infusate (or the absence of air); no echo received within the pulse window is interpreted as indicating the presence of air (or the absence of infusate). The sensor 38 operates identically. This sensor arrangement provides a single point of sensor contact for transmitting and receiving.

Figure 26:
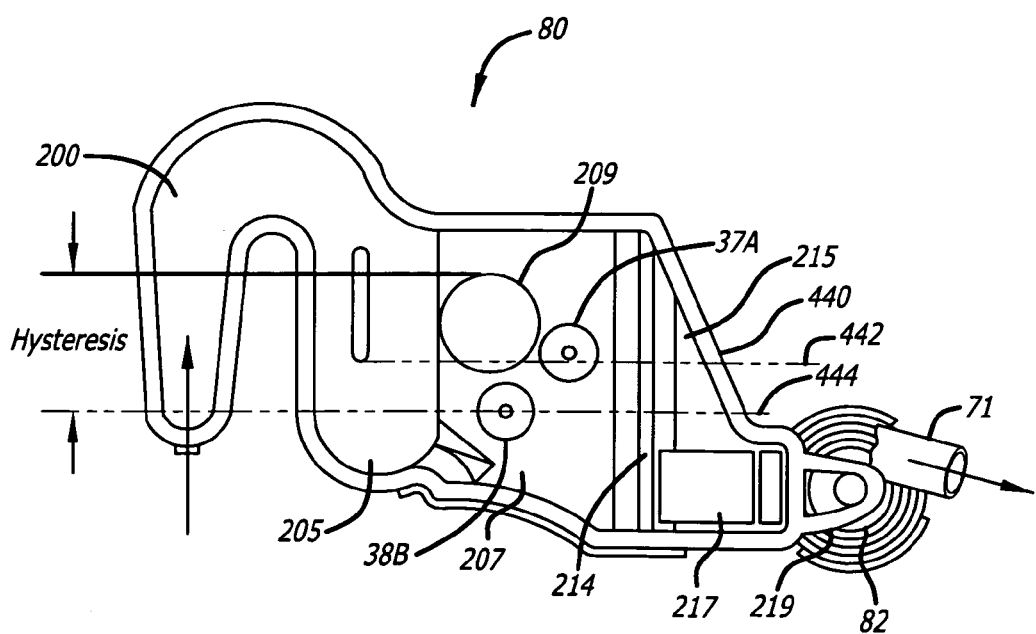
FIG. 26 is a schematic diagram of the bubble trap seen in FIG. 10 with a hydrophobic membrane for venting air.

Preferably, air management in the bubble trap is based upon venting air through a hydrophobic membrane in contact with infusate flowing through the bubble trap. In FIG. 26, the transition 214 between the laminar flow and outlet chambers 207, 215 includes a downwardly angled wall 440. The sensors 37 and 38 have fields of view through the sensor couplers 37A and 38A into the laminar flow chamber 207. The level line 442 is centered in the field of view of the sensor 37, and the level line 444 is centered in the field of view of the sensor 38. The level line 442 passes through the lower quadrant of the hydrophobic membrane 209, and the level line 444 is parallel to the level line 442, below the hydrophobic membrane 209, but above the riser 219 through which infusate flows to the valve 82 and then to the output port 71. As air collects in a pocket in the upper reaches of the bubble trap, the border between the air pocket and infusate moves down the downwardly angled wall 440; when the border moves downwardly across the hydrophobic membrane 209, air is vented from the air pocket through the membrane. When the border between the air pocket and infusate is above a level line 442 or 444, the sensor 37 or 38 associated with the respective level line senses fluid; when the border is below a level line 442 or 444, the sensor 37 or 38 associated with the respective level line senses air. An advantage of the sensor locations is that the increased velocity of the laminar sheet of infusate through the laminar flow chamber 207 sweeps bubbles from the fields of view of the sensors 37 and 38. This reduces the risk of either sensor 37 or 38 producing false level indications in response to bubbles.

Figure 27:
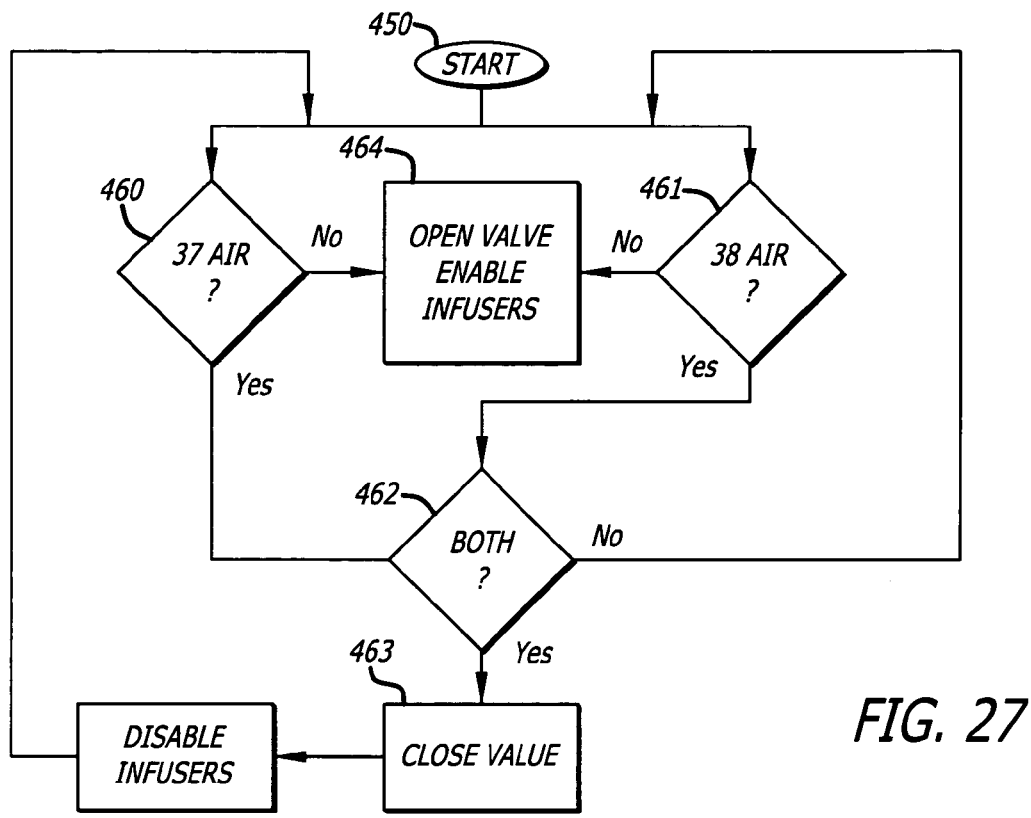
FIG. 27 is a flow diagram illustrating a logic control mechanization to control flow through the bubble trap illustrated in FIG. 26.

The preferred air management logic control mechanization for the sensors disposed with respect to the bubble trap as in FIG. 26 is shown in FIG. 27; this logic represents an adaptation of the air control loop 360 of FIG. 24 for the case of two sensors. The logic of FIG. 27 controls the state of the valve 82 and enablement of the pressure infusers 18 according to whether the sensors 37 and 38 report the presence of infusate or air in the bubble trap. Initially, the heat exchanger is primed at 450, when the fluid container 62 and the bubble trap 80 are empty. The sensors 37 and 38 both report the presence of air at 460 and 461, satisfying the test at 462. The valve 82 is closed and the pressure infusers 18 are disabled at 463. The logic loops through 460, 461, 462 and 463 until either sensor 38 or 37 reports the presence of infusate (or, conversely, no air). When the presence of infusate is reported at 460 or 461 the valve 82 is opened and the operator is given an indication to activate inflation of a balloon in a pressure infuser 18 at 464. Then both sensors are monitored for air. When both sensors report air, the valve 82 is closed and the operating pressure infuser is deactivated at 463, and the logic again loops until infusate is reported by either or both sensors as previously mentioned.

When the valve 82 is closed in response to the test at 462, the bubble trap is again primed with infusate, which will rise in the bubble trap, first passing the lower sensor 38. In some aspects, the logic of FIG. 27 may utilize a time delay to the negative exit of the test at 461, thereby prolonging the closure of the valve 82 while the bubble trap primes. In these instances, the use of two sensors provides hysteresis in the operation of the valve 82.

Figure 28:
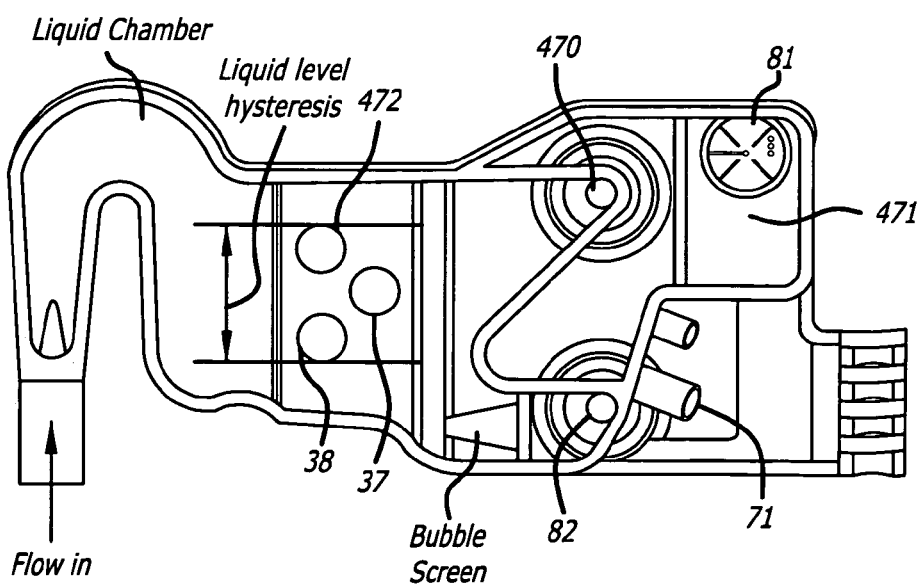
FIG. 28 is a schematic diagram of a second bubble trap embodiment.

Other air sensing and management configurations for the bubble trap 80 are possible. One such configuration, shown in FIG. 28 as an adaptation of the bubble trap 80, uses a second solenoid driven valve 470 to isolate the air vent 81 in an air chamber 471 in order to keep the hydrophobic membrane 209 dry. If either of the sensors 37 and 38 senses infusate, the valve 82 is open. If both sensors 37 and 38 sense air, the valve 82 is closed. If either of the sensors 37 and 472 senses the presence of infusate, the valve 470 remains closed. If both sensors 37 and 472 sense the presence of air, the valve 470 is opened. The pressure of infusate flowing into the bubble trap 80 from the fluid container forces the air into the air chamber 471 where it is vented through the hydrophobic membrane 209. The level of infusate rises as air exits into the air chamber 471, and the valves 82 and 470, respectively, open and close when the sensors 37, 38, and 472 once again sense the presence of infusate. A third ultrasonic sensor to sense the contents of the bubble trap 80 through coupler location 472 may be included in order to provide greater redundancy, a larger degree of hysteresis, and a richer functional set than the two sensors 37 and 38. One additional function realized by the addition of a third sensor is to open the valve 470 at some intermediate infusate level while holding open the valve 82 in order to vent air while continuing to deliver infusate to a patient.

Although a heat exchanger for high flow rate infusion unit has been described with reference to a number of embodiments, it should be understood that various modifications can be made without departing from the principles of this specification, which are limited only by the following claims.

The invention claimed is:

1. A heat exchanger for heating fluids, comprising:
   a fluid container with near and distal ends, two edges, and a planar, non-sinuous laminar flow path with an inlet and an outlet;
   a housing attached to the fluid container at the near end; and,
   first and second rails attached to the housing, each rail positioned in the fluid container near and parallel to a respective edge thereof such that the laminar flow path is between the rails;
   in which, the first rail has a straw like construction including a first fluid passageway that opens to the inlet of the laminar flow path, and the second rail includes a second fluid passageway that opens to the outlet of the laminar flow path.

2. The heat exchanger of claim 1, in which the inlet of the laminar flow path is near the distal end of the fluid container and the outlet of the laminar flow path is near the near end of the fluid container.

3. The heat exchanger of claim 2, in which the first rail includes first and second ends, the first fluid passageway opens through the first end, and a slot near the second end opens between the first fluid passageway and the inlet of the laminar flow path.

4. The heat exchanger of claim 2, in which the second rail includes first and second ends, the second fluid passageway opens through the first end, and a slot opens between the second fluid passageway and the outlet of the laminar flow path.

5. The heat exchanger of claim 4, in which the first rail includes first and second ends, the first fluid passageway opens through the first end, and a slot near the second end opens between the first fluid passageway and the inlet of the laminar flow path.

6. The heat exchanger of claim 5, in which the first ends of the first and second rails are attached to the housing.

7. The heat exchanger of claim 2, in which an inlet port of the fluid container at a first end of the first rail is in fluid communication with the first fluid passageway and an outlet port of the fluid container at a first end of the second rail is in fluid communication with the second fluid passageway.

8. The heat exchanger of claim 7, in which the first ends of the first and second rails are attached to the housing.

9. The heat exchanger of claim 1, further including a curve in the fluid container for funneling fluid toward the outlet of the laminar flow path.

10. The heat exchanger of claim 9, in which an inlet port of the fluid container at a first end of the first rail is in fluid communication with the first fluid passageway, and an outlet port of the fluid container at a first end of the second rail is in fluid communication with the second fluid passageway.

11. A method for operating an infusion unit including a pair of opposed heating plates defining space therebetween for receiving a fluid container, by:

placing a heat exchanger fluid container in the space between the heating plates;

causing fluid to flow through a central rail passageway in a straw like first rail positioned at and parallel to a first edge of the fluid container into a flow path inlet;

spreading fluid from the flow path inlet into a planar, non-sinuous laminar flow path in the fluid container;

causing the fluid in the laminar flow path to flow to a flow path outlet in the fluid container; and, causing fluid to flow from the flow path outlet through a second rail passageway positioned at and parallel to a second edge of the fluid container.

12. The method of claim 11, in which causing fluid to flow from the flow path outlet through a second rail passageway of the fluid container includes causing the fluid to flow along a curve in the fluid container, into the flow path outlet.

13. The method of claim 11, further including applying heat to the fluid container through the opposed heating plates.

* * * * *

UNITED STATES PATENT AND TRADEMARK OFFICE
CERTIFICATE OF CORRECTION

| | | |
|---|---|---|
| PATENT NO. | : 8,385,731 B2 | Page 1 of 1 |
| APPLICATION NO. | : 13/135278 | |
| DATED | : February 26, 2013 | |
| INVENTOR(S) | : Randall Charles Arnold | |

It is certified that error appears in the above-identified patent and that said Letters Patent is hereby corrected as shown below:

In the Drawings:

Sheet 11 of 23 (Fig. 13)
Line 12 (approx.); Delete "640" and insert -- 64o --, therefor.

Sheet 21 of 23(Reference Numeral 420)(FIG. 24)
Line 1; Delete "DISCLODGE" and insert -- DISLODGE --, therefor.

Sheet 21 of 23(Reference Numeral 392)(FIG. 24)
Line 1; Delete "VALUE" and insert -- VALVE --, therefor.

Sheet 21 of 23(Reference Numeral 394)(FIG. 24)
Line 1; Delete "VALUE" and insert -- VALVE --, therefor.

Sheet 23 of 23(Reference Numeral 463)(FIG. 27)
Line 1; Delete "VALUE" and insert -- VALVE --, therefor.

In the Specifications:

Column 1
Line 6; After "of" delete "co-pending".
Line 51; Delete "PCT/US20000/02630," and insert -- PCT/US2000/02630, --, therefor.

Column 2
Line 5-6; Delete "ANESTHESEOLOGY" and insert -- ANESTHESIOLOGY --, therefor.

Column 8
Line 15; Delete "fine" and insert -- line --, therefor.

Signed and Sealed this
Ninth Day of July, 2013

Teresa Stanek Rea
*Acting Director of the United States Patent and Trademark Office*